US009205035B2

(12) United States Patent
Engqvist et al.

(10) Patent No.: US 9,205,035 B2

(45) Date of Patent: Dec. 8, 2015

(54) ION SUBSTITUTED CALCIUM PHOSPHATE PARTICLES

(75) Inventors: Hakan Engqvist, Osthammar (SE); Wei Xia, Uppsala (SE)

(73) Assignee: PSILOX AB, Uppsala (SE)

( * ) Notice: Subject to any disclaimer, the term of this patent is extended or adjusted under 35 U.S.C. 154(b) by 948 days.

(21) Appl. No.: 13/389,075

(22) PCT Filed: Aug. 4, 2010

(86) PCT No.: PCT/SE2010/050874

§ 371 (c)(1), (2), (4) Date: Feb. 6, 2012

(87) PCT Pub. No.: WO2011/016772

PCT Pub. Date: Feb. 10, 2011

(65) Prior Publication Data

US 2012/0134919 A1 May 31, 2012

(30) Foreign Application Priority Data

Aug. 4, 2009 (SE) ........................................ 0901059

Apr. 26, 2010 (SE) ........................................ 1050414

(51) Int. Cl.

| | |
|---|---|
| ***A61K 9/14*** | (2006.01) |
| ***A61K 8/24*** | (2006.01) |
| ***A61K 6/033*** | (2006.01) |
| ***A61L 27/12*** | (2006.01) |
| ***A61Q 11/00*** | (2006.01) |
| ***C01B 25/32*** | (2006.01) |
| ***A61K 8/02*** | (2006.01) |
| *A61K 6/00* | (2006.01) |

(52) U.S. Cl.

CPC ................ *A61K 8/24* (2013.01); *A61K 6/0017* (2013.01); *A61K 6/0038* (2013.01); *A61K 6/033* (2013.01); *A61K 8/025* (2013.01); *A61K 8/0279* (2013.01); *A61L 27/12* (2013.01); *A61Q 11/00* (2013.01); *C01B 25/32* (2013.01); *A61K 6/0082* (2013.01); *A61K 2800/412* (2013.01); *A61K 2800/56* (2013.01)

(58) Field of Classification Search

CPC .................................................... A61K 6/0082

See application file for complete search history.

(56) References Cited

U.S. PATENT DOCUMENTS

| | | |
|---|---|---|
| 5,702,677 A | 12/1997 | Shimp et al. |
| 5,858,318 A | 1/1999 | Luo |
| 6,312,468 B1 | 11/2001 | Best et al. |

(Continued)

FOREIGN PATENT DOCUMENTS

| | | |
|---|---|---|
| CN | 101376035 A | 3/2009 |
| GB | 2316940 A | 3/1998 |

(Continued)

OTHER PUBLICATIONS

Okazaki, Differences in solubility of two types of heterogeneous fluoridated hydroxyapatites, Biomaterials, 1998, 19, 611-616.*

(Continued)

*Primary Examiner* — Paul Dickinson

(74) *Attorney, Agent, or Firm* — Young & Thompson

(57) ABSTRACT

A method for formation of spherical particles of ion substituted calcium phosphate. The method is based on precipitation of particles from a buffered solution under static, stirring or hydrothermal conditions. Also, the use of the formed materials and the particles in itself.

17 Claims, 12 Drawing Sheets

(56) References Cited

U.S. PATENT DOCUMENTS

| | | | |
|---|---|---|---|
| 7,326,464 | B2 | 2/2008 | Lemaitre et al. |
| 2008/0260714 | A1 | 10/2008 | Barry et al. |
| 2008/0317807 | A1 | 12/2008 | Lu et al. |

FOREIGN PATENT DOCUMENTS

| | | | |
|---|---|---|---|
| JP | 2000-042096 | | 2/2000 |
| JP | 2000-517281 | | 12/2000 |
| WO | 2005082780 | A1 | 9/2005 |
| WO | 2007137606 | A1 | 12/2007 |
| WO | 2010113800 | A1 | 10/2010 |

OTHER PUBLICATIONS

Miyaji F. et al: "Formation and structure of zinc-substituted calcium hydroxyapatite", In: Materials Research Bulletin, 2005, vol. 40, Nr. 2, pp. 209-220.
Bigi A. et al: "Strontium-Substituted Hydroxyapatite Nanocrystals", In: Inorganica Chimica Acta, 2007, vol. 360, pp. 1009-1016.
Okazaki M. et al: "Differences in Solubility of Two Types of Heterogeneous Fluoridated Hydroxyapatites", In: Biomaterials, 1998, vol. 19, pp. 611-616.
Bigi A. et al: "Magnesium Influence on Hydroxyaptite Crystallisation", In: Journal of Inorganic Biochemistry, 1993, vol. 49, No. 1, pp. 69-78.
Hofmann, I. et al: "Precipitation of Carbonated Calcium Phosphate Powders from a Highly Supersaturated SBF Solution", In: Key Engineering Materials, 2007, vols. 330-332, pp. 59-62.
Sandin K. et al: "Formation of carbonated apatite particles from a supersaturated inorganic blood serum model", In: Journal of Materials Science: Materials in Medicine, 2009, vol. 20, Nr. 8, pp. 1677-1687.
Medvecky L. et al: "Influence of manganese on stability and particle growth of hydroxyapatite in simulated body fluid", In: Colloids and Surfaces A: Physicochemical and Engineering Aspects, 2006, vol. 281, Nr. 1-3, pp. 221-229.
Barralet J. et al: "Carbonate substitution in precipitated hydroxyapatite: An investigation into the effects of reaction temperature and bicarbonate ion concentration", In: Journal of Biomedical Materials Research, 1998, vol. 41, Nr. 1, pp. 79-86.
Garcia C. et al: "Effect of Some Physical-Chemical Variables in the Synthesis of Hydroxyapatite by the Precipitation Route", In: Key Engineering Materials, 2005, vols. 284-286.
Tonegawa T. et al: "Synthesis and characterization of metal ions containing hydroxyapatite microparticles with high specific surface area", In: J. of Nanoscience and Nanotechnology, 2007, vol. 7, pp. 839-843.
Tadic D. et al: "Continuous synthesis of amorphous carbonated apatites", In: Biomaterials, 2002, vol. 23, pp. 2553-2559.
Luo, P. et al: "Preparing Hydroxyapatite Powders with Controlled Morphology",In: Biomaterials, 1996, vol. 17, No. 20, pp. 1959-1964.
Bracci B. et al: "Effect of Mg2+, Sr2+, and Mn2+ on the chemico-physical and in vitro biological properties of calcium phosphate biomimetic coatings", In: Journal of Inorganic Biochemistry, 2009, vol. 103, pp. 1666-1674.
Boanini E. et al: "Ionic substitutions in calcium phosphates synthesized at low temperature", In: Acta Biomaterialia, 2010, vol. 6, pp. 1882-1894.
Gross K. et al: "Sintered hydroxyfluorapatites. Part I: Sintering ability of precipitated solid solution powders", Biomaterials 25 (2004) 1375-1384.
Hench L.: "Bioceramics: From Concept to Clinic", In. J. Am. Ceram. Soci. 1991, vol. 74 (7), pp. 1487-1510.
Hui G. Z. et al: "Morphologically Controlled Synthesis of Hydroxyapatite with Partial Substitution of Fluorine", In: Chem. Mater. 2005, vol. 17, pp. 5834-5830.
Landi E. et al: "Sr-substituted hydroxyapatites for osteoporotic bone replacement", In: Acta Biomaterialia 2007, vol. 3 , pp. 961-969.
Pietak, A. et al: "Silicon substitution in the calcium phosphate bioceramics", In: Biomaterials, 2007, vol. 28 , pp. 4023-4032.
Robinson, C. et al: "The Chemistry of Enamel Caries", In: Critical Reviews in Oral Biology & Medicine, 2000, vol. No. 4, pp. 481-495.
Xu A. et al: "Biomimetic mineralization", In: Journal of Materials Chemistry, 2007, vol. 17, pp. 415-449.
International Search Report, dated Oct. 28, 2010, in PCT/SE2010/050874.
Zhang et al., "Morphologically Controlled Synthesis of Hydroxyapatite with Partial Substitution of Fluorine," Chem. Mater. 2005, 17, pp. 5824-5830.

* cited by examiner (a) (b) (c)

ION SUBSTITUTED CALCIUM PHOSPHATE PARTICLES

TECHNICAL FIELD OF THE INVENTION

The present invention relates to method for manufacture of ion substituted calcium phosphate nanoparticles, and in particular calcium phosphate nanoparticles, with controlled morphology and structure. The invention also relates to such a material composition to be used in medical applications.

BACKGROUND OF THE INVENTION

Calcium phosphates (CaP) and in particular hydroxyapatite ($Ca_{10}(PO_4)_6(OH)_2$, HA), is a mineral that is widely used in medical applications due to its similarity to the mineral components of bone and teeth and its biocompatibility. Furthermore hydroxyapatite is non-toxic, biocompatible and bioactive. This means that hydroxyapatite is not harmful and not recognized as a foreign body and on the other hand that it may have positive effects on remodelling of bone. Hence hydroxyapatite has been widely used in bone repair and as drug/gene delivery vehicle, catalyst, ion adsorption/exchange agent, photoelectric regent, etc. Resorbable nanoparticles (i.e. particles that can be dissolved in vivo) are of special interest for a number of applications, e.g. bone void fillers, drug delivery vehicle, desensitization of dentin tubuli, etc.

Hydroxyapatite in bone is a multi-substituted calcium phosphate, including traces of $CO_3^{2-}$, $F^-$, $Cl^-$, $Mg^{2+}$, $Sr^{2+}$, $Si^{4+}$, $Zn^{2+}$, $Ba^{2+}$, $Fe^{3+}$, etc. These ionic substitutions play an important role in bone formation and normal functions, such as the solubility, the crystal structure and the surface chemistry of the material.

Fluoride exists in bone and teeth of vertebrate bodies. It was reported that the substitution of fluoride for OH sites and formation of fluoride-substituted hydroxyapatite enhanced the acid resistance and the mechanical properties of hydroxyapatite bioceramics (Gross et al., Biomaterials 2004; 25:1375-1384), and induced better biological response (Robinson et al., Crit Rev Oral Biol Med 2000; 11:481-495).

Silicon has been found to be essential for normal bone and cartilage growth and development. Synthetic calcium phosphate that includes trace levels of Si in their structures demonstrate markedly increased biological performance in comparison to stoichiometric calcium phosphate (Pietak et al., Biomaterials 2007; 28:4023-4032). The improvement in biological performance can be attributed to Si-induced changes in the material properties and also to the direct effects of Si in physiological processes of the bone and connective tissue systems. Si substitution promotes biological activity by the transformation of the material surface to a biologically equivalent calcium phosphate by increasing the solubility of the material, by generating a more electronegative surface and by creating a finer microstructure. Release of Si complexes to the extracellular media and the presence of Si at the material surface may induce additional dose-dependent stimulatory effects on cells of the bone and cartilage tissue systems.

Because strontium is chemically and physically closely related to calcium, it is easily introduced as a natural substitution of calcium in calcium phosphate. Strontium has proved to have the effects of increasing bone formation and reducing bone resorption, leading to a gain in bone mass and improved bone mechanical properties in normal animals and humans. Sr substituted hydroxyapatite ceramics have exhibited better mechanical properties than pure hydroxyapatite, and enhanced the proliferation and differentiation of osteoblast cells in in vitro study (Landi et al., Acta Biomaterials 2007; 3:961-969). The positive effect of strontium-ions is used in a pharmaceutical, called strontium ranelate, which is applied to people with osteoporosis.

Methods to produce pure CaP particles, spherical granules and bulk materials have been described in the prior art and include wet chemical precipitation, sol-gel or hydrothermal synthesis, as described in e.g. U.S. Pat. Nos. 5,858,318, 7,326,464, 5,702,677 and Hui Gang Zhang, Qingshan Zhu, Yong Wang, *Chem. Mater.* 2005, 17, 5824-5830.

In other processes, the synthesis of calcium phosphate mimic biomineralization, which is a natural self-assembly process by which this kind of mineral is formed in living organisms. Moreover, synthesis of mineral nanomaterials with specific morphologies and structures from a solution attracts increasing attention because of their unique physical, chemical and biological properties and potential applications in advanced functional materials.

Current synthesis of mineral nanomaterials with different morphologies, such as spheres, fibers and rods, core-shell structures and mesoporous structures, mimicking a biomineralization process, are concentrated on self-assembly using surfactants and biomolecules (Xu et al, J Mater Chem 2007; 17:415-449). For example, the nucleation and growth of calcium phosphate can be controlled by some specific surfactants or biomolecules that direct the growth and hence control the morphology of the grown nanomaterials. Without surfactants, the morphology is inherently controlled by the crystals preferentially growing on a specific crystal plane with lowest surface tension in the solution. For example, in a supersaturated solution (usually comprising calcium and phosphate ions) calcium phosphate spontaneously grows like flakes or fibers/rods, which are oriented along the crystals c axis.

Not all morphologies are convenient to serve as delivery particles, catalyst support, ion adsorption/exchange agent, etc., until now when for example rod, tubular, sheet or spherical shaped nanoparticles have been investigated. By way of example, to make a drug delivery process efficient, high surface areas and porous structures are advantageous to adsorb as much active substance as possible and, of course, there is as well the requirement of biocompatibility and a bond between carrier and substance.

One problem for the preparation of CaP particles is to control size distribution and shape of the particles. Often the size distribution is wide and caused by the hexagonal symmetry and the lattice parameters of CaP. Most likely an orientation along the c-axis and therewith a pin-like shape occurs.

SUMMARY OF THE INVENTION

In view of the foregoing one object of the invention is to provide calcium phosphate (CaP) particles in the nano- to micrometre range with controlled morphology and this without using surfactants or templates.

Hence the present invention provides a method for manufacturing of ion-substituted CaP particles with controlled morphology and structure via a surfactant-free biomineralization process, the CaP particles and its use in biomedical applications and as drug carrier as defined in the independent claims.

In a method in accordance with the invention CaP particles with controlled morphology and morphology are prepared in a biomimetic process without surfactants.

For the preparation of CaP particles with controlled morphology and morphology in accordance with the invention, the aim is to use precursors with compositions like they exist in nature and to use no chemicals that are not used in the natural processes and that should as well not be included in the product, i.e. in the manufacturing method of the invention no surfactants have to be used in the particle synthesis. In prior art methods organic surfactants or templates like, urea, collagen, monosaccharide or $Na_2EDTA$ are used to achieve spherical structures through limited reaction spaces. The use of surfactants leads to many steps in the production and further steps, for example heat treatment, could be necessary to remove the organic components from the CaP. Additionally, residuals may lead to problems when used in vivo. One advantage of the present invention is that due to a biomimetic manufacturing method these further steps are not necessary and the process is thereby simplified. In addition, one advantage of using ion substitution for control of the morphology is that this enables other shapes and porosity not readily enabled by surfactant controlled processes.

In the method of the invention the particles are synthesised with mineralisation and precipitation methods comprising the basic steps of preparing a salt solution and precipitating CaP particles from the salt solution.

In more detail the method comprises the steps of:

providing an aqueous solution comprising one or more of calcium ions, sodium ions, potassium ions, chloride ions and/or phosphate ions, the solution having an initial pH in the range of 2.0 to 10.0, preferably a pH between 6.0 and 8.0, and a temperature of 20° C. to 150° C., the solution further comprising one or more of the substitution ions magnesium, strontium, silicon, fluoride, barium, iron and zink, carbonate ions and sulphate ions or combinations thereof, and providing a self-assembled process in the form of a static process, a stirring process and/or a hydrothermal process for a period of time sufficient for the formation of the desired nanoparticles.

In a preferred embodiment of the invention the solution comprises calcium, and phosphate ions and one or more of magnesium, sodium, potassium, chloride, carbonate or sulphate ions wherein the concentration of said ions are, the concentration of calcium ions can be in the range 0.01-25 $10^{-3}$M, the concentration of magnesium ions can be in the range 0.01-15 $10^{-3}$M, the concentration of sodium ions can be in the range 0.01-1420 $10^{-3}$M, the concentration of potassium ions can be in the range 0.01-1420 $10^{-3}$M, the concentration of chloride ions can be in the range 0.01-1030 $10^{-3}$M, the concentration of phosphate ions can be in the range 0.01-10 $10^{-3}$M, the concentration of carbonate ions can be in the range 0.01-270 $10^{-3}$M, the concentration of sulphate ions can be in the range 0.01-5 $10^{-3}$M, the concentration of the substitution ions could be in the range of 0.01-1.0 $10^{-3}$M for $Sr^{2+}$, 0.01-10 $10^{-3}$M for $Si^{4+}$ and 0.01-0.5 $10^{-3}$M for $F^-$.

In one embodiment the manufacturing method utilizes a supersaturated phosphate buffered solution comprising at least calcium ions and substitution ions, for example $Sr^{2+}$, $Si^{4+}$, $F^-$ $Mg^{2+}$, $Zn^{2+}$, $Ba^{2+}$ or $Fe^3$ or combinations thereof. The surfactant-free self-assembled process takes place in the buffer solution, and the dynamic formation rate can be controlled by temperature, pH, composition and ion concentration. The self-organized process can be in a static process, a stirring process, and a hydrothermal process. The formation time is typically within 1 h to 4 weeks, for example more than 2 hours or more than 5 hours or more than 10 hours or more than 1 day but less then 4 weeks or less than 2 weeks or less then 1 week, but longer or shorter formation times can also form particles.

In one embodiment of the present invention at least one of the substitution ions is $Sr^{2-}$.

In another embodiment of the present invention at least one of the substitution ions is $Mg^{2+}$.

In another embodiment of the present invention at least one of the substitution ions is $Si^{4+}$.

In another embodiment of the present invention at least one of the substitution ions is $F^-$.

In another embodiment of the present invention at least two of the substitution ions are $Sr^{2+}$ and $Mg^{2+}$.

In another embodiment of the present invention at least two of the substitution ions are $Sr^{2+}$ and $F^-$.

In another embodiment of the present invention at least two of the substitution ions are $Mg^{2+}$ and $F^-$.

In another embodiment the temperature of the solution is 30° C. to 70° C.

In yet another embodiment the magnesium concentration in the formed particle is between 0 and 10% by weight, for example more than 1% or more than 3% or more than 5% or 10% or less than 8% or less than 5%.

In one embodiment the method comprises the step of growth and self-assembly of the particles in the solution, whereby ion-substituted particles with a hollow core and a dense shell or, a hollow core and a porous shell or, a porous core and a dense shell or, the particles are porous are formed due to adjustment of the concentration of the substitution ions in the solution.

In yet another embodiment, the ion-substituted particles are spherical.

In yet another embodiment the concentration of $Sr^{2+}$ in the solution is less than 0.15 mM, preferably about 0.06 mM, whereby irregular spherical porous Sr substituted nanoparticles with a diameter of about 1 μm are formed.

In yet another embodiment the concentration of $Sr^{2+}$ in the solution is more than 0.06 mM and less than 0.3 mM, preferably about 0.15 mM, whereby spherical porous Sr-substituted nanoparticles with a diameter of 100-300 nm, each nanoparticle having a hollow core and a porous shell, are formed.

In yet another embodiment the concentration of $Sr^{2+}$ in the solution is more than 0.15 mM and less than 0.6 mM, preferably about 0.3 mM, whereby regular spherical Sr-substituted nanoparticles with a diameter of 200-500 nm, each nanoparticle having a hollow core and a porous shell, are formed.

In yet another embodiment the concentration of $Sr^{2+}$ in the solution is 0.3 mM and less than 0.67 mM, preferably about 0.6 mM, whereby Sr-substituted spherical nanoparticles with a diameter of 100-500 nm, each nanoparticle having a dense shell and a porous core, are formed.

In yet another embodiment the $Sr^{2+}$ concentration is from 0.01 to 0.7 mM for example 0.01 or more than 0.05 or more than 0.1 or more than 0.3 or 0.7 or less or less then 0.5 mM; and the $Mg^{2+}$ concentration is from 0.1 to 0.5 mM, for example 0.1 or more than 0.2 or more than 0.3 or 0.5 or less then 0.4 mM.

In yet another embodiment the concentration of $F^-$in the solution is about 0.04-0.2 mM, whereby spherical porous F-substituted nanoparticles with a diameter of 300 500 nm are formed.

In yet another embodiment the concentration of $Si^{4+}$ is about 6 mM, whereby porous Si-substituted nanoparticles with a size of 200-500 nm are formed.

In a first aspect of the invention particles with controlled morphology, such as hollow or porous CaP particles or combinations thereof are provided. For example the particle may have a hollow core and a dense shell, or a hollow core and porous shell, or a porous core and a dense shell, or the particle may be porous. The morphology of the CaP particles of the invention can be controlled via adjusting the concentration of substituted ions in the growth solutions. The diameter of the spherical particles of the invention is preferably 10-1000 nm, for example more than 30 nm or more than 50 nm or more than 100 nm but less than 1000 nm or less than 500 nm or less than 300 nm. The formed particles are not single crystals but composed of several smaller units, fully or partially or non-crystalline, of ion substituted CaP. The smallest unit of the particles can for example be flake-like nanoparticles and needle-like nanoparticles formed together to a larger particle.

In one embodiment the formed particles are heat treated, for example above 30° C. or above 50° C. or above 100° C.

In another embodiment the strontium in the formed particle concentration is between 0 to 35% by weight, for example more than 5% or more than 15% or more than 25% or 35% or less than 30% or less than 20% or less than 10%.

In yet another embodiment the particle is hollow and/or porous.

In yet another embodiment the particle has a porous core with a dense shell.

In another embodiment the particle comprises one or more of $Sr^{2+}$, $Si^{4+}$, and $F^-$ as substitution ions.

The morphology of particles prepared using the method according to the present invention is being controlled with diverse design. Solid, porous, hollow or rope-like structured spheres with diameters from 100 nm to 1 μm can be formed. Magnesium, fluor, silicon and the liquid precursor (buffer solution), alone or in combination, in addition to strontium may strongly influence the morphology.

In one embodiment of the invention porous and/or hollow, strontium-doped, spherical calcium phosphate particles are provided.

In another embodiment fluoride and/or silicon-doped spherical calcium phosphate particles are provided.

In a second aspect of the invention particles for controlled ion release, such as strontium release, from the prepared particles in human or simulated body environment are provided.

Through a strontium release study using particles according to the present invention a dependency of the released amount of ions on the pH value was shown. A decrease of pH value of the immersion liquid from 8.0 to 6.8 was found to double the released amount of strontium and totally 20% of the incorporated strontium was released after 13 days without change of the solution. Furthermore, the presence of inorganic ions in the immersion liquid decreased the strontium content in the solution, respectively induced crystallisation of CaP on the particles, this shows that the particles are bioactive (Hench L L. J Am Ceram Soc 1991;74:1487-1510). This feature is especially important for applications where remineralising properties is of importance, e.g. dental and orthopaedic applications.

The ability of CaP to form non-stoichiometric crystals with controlled morphology enables to tailor materials for specific applications as for example the regeneration of damaged bone could be stimulated by inserting biocompatible, biodegradable, artificial prepared, ion-substituted CaP into the body and thus augment the strength of the bones. However not limited to this, the wide range of particle morphologies and compositions that can be produced with the invention opens up for several applications:

Drug delivery with sustained and controlled release behaviour. Non-limiting examples of drugs includes antibiotics, anti-inflammatory, proteins, cancer treatment and drugs for the treatment of pain. The drug loading can be performed using any method known to a person skilled in the art. Non-limiting examples includes soaking and loading during the manufacture of the particles or a combination of the two. For example, CaP particles of the invention may enable efficient drug delivery by having a large surface area and a porous structure, which makes it possible to adsorb a large amount of active substance, while fulfilling requirement of biocompatibility and a strong bond between carrier and substance.

The particles can be used in bone repair and regeneration. The particles can be delivered to the bone defect using the methods known to a person skilled in the art. Two non-limiting examples include soaking of the particles in blood plasma and adding them to the defect, or delivery of the particles using a carrier liquid or gel via a syringe. Said gel may be a polysaccharide such as hyaluronan or chitosan or any derivative thereof. Other examples include glycerol, polyethylene glycol or other water-miscible liquids. In addition the particles can be added to injectable self hardening material systems, non limiting examples include injectable bioceramics (calcium phosphate cements, calcium sulphate cements, calcium silicate cements and the like) and to non resorbable injectable polymers like poly-metyl-meta-acrylates (PMMA). To further improve the regeneration, the particles and/or the liquid or gel may additionally comprise biological substances such as growth factors.

The particles can be used in tooth repair and regeneration. The particles can be delivered to the bone defect using the methods known to a person skilled in the art. Two non-limiting examples include soaking of the particles in blood plasma and adding them to the defect, or delivery of the particles using a carrier liquid or gel via a syringe. Said gel may be a polysaccharide such as hyaluronan or chitosan or any derivative thereof. Other examples include glycerol, polyethylene glycol or other water-miscible liquids. In addition the particles can be added to injectable self hardening material systems, non limiting examples include injectable bioceramics (calcium phosphate cements, calcium sulphate cements, calcium silicate cements and the like) and to non resorbable injectable polymers like poly-metyl-meta-acrylates (PMMA). To further improve the regeneration, the particles and/or the liquid or gel may additionally comprise biological substances such as growth factors.

Dental minimally invasive and preventative treatments such as cleaning, polishing, whitening, bleaching and blasting teeth, sealants, cavity prevention, tooth preservation and restorations, and to improve the surface of the enamel after bleaching.

For treatment of peridontitis using a carrier gel or liquid, or as a cavity restoration or as part of cavity filling restoration For treatment of peri-implantatis (filling and regeneration of bone voids around dental implants formed due to peri-implantitis). Here the CaP particles can be delivery to the site using the delivery mechanisms for injectable formulations or mixed with blood or the like and packed into the defect.

Filler particles in toothpaste for healing of sensitive tooth roots, to desensitization of open tubulis and healing of early caries. Preferably using spherical CaP particles, even more preferred spherical CaP particles containing F-ions.

Adsorption agent for heavy metal ions.

Delivery of genes, growth factors, contrast substances, radiolabled particles or substances or drugs.

Desensitization of dentine tubulis. Hollow and/or porous particles are suitable to fill the open dentine tubulis.

Dental tape, dental tooth bleaching tapes or paste for healing of enamel.

Tooth paste, mouth water, mouth wash, mouth spray, tooth cream, bleaching and whitening pastes.

Food supplement and chewing gum. For the chewing gum CaP particles in the order of about 10 wt. % or below is added to achieve remineralising properties.

The particles of the present invention may be combined with other material to improve the properties for example filler particles in injectable biomaterials. Non-limiting examples includes: PMMA bone cements, bioceramics (e.g. calcium phosphates, calcium sulphates), glass ionomer cements.

For drug delivery, the first and second aspect of the invention mentioned above results in a first approach where the particle morphology is adapted to enable loading of the drug in pores or hollows in the particles, and a second approach comprising controlled ion release, respectively. In the first approach the drug may be loaded after growth and/or during growth.

Like the F-substituted particles of FIG. 9 the surface of the Si-substituted particles of FIG. 10 is comparatively rough and comprises flakes protruding from the surface. However, the F-substituted particles have a more regular spherical shape. Both these substituted particles would be suitable for drug-delivery, gene delivery, protein adsorption and filler material in chromatographic columns.

Embodiments of the invention are defined in the dependent claims. Other objects, advantages and novel features of the invention will become apparent from the following detailed description of the invention when considered in conjunction with the accompanying drawings and claims.

BRIEF DESCRIPTION OF THE DRAWINGS

Preferred embodiments of the invention will now be described with reference to the accompanying drawings, wherein

FIG. 9' shows SEM images of 0.6 mM Sr-doped porous CaP spheres with increasing Ca/P ratios aged at 100° C. for 24 hours. Ca/P ratios are (A) 0.1, (B) 1.0, (C) and (D) 2.5, (E) and (F) 5.0.

FIG. 10' shows SEM images of fluoride substituted calcium phosphate nanospheres prepared from a phosphate buffer solution treated at 100° C. containing 0.2 mM fluoride ion for (A) 12 hours and (B) 24 hours, and 0.15 mM silicate ion for (C) 12 hours and (D) 24 hours.

FIG. 11 shows the morphology of calcium phosphate aged at 60° C. for 1 week with increasing strontium concentration from 0 to 0.6 mM in (A) to (E). The Ca/P ratio is 0.1. Arrows in (D) indicate the hollow nature of the particles.

DETAILED DESCRIPTION OF EMBODIMENTS

Figure 1:
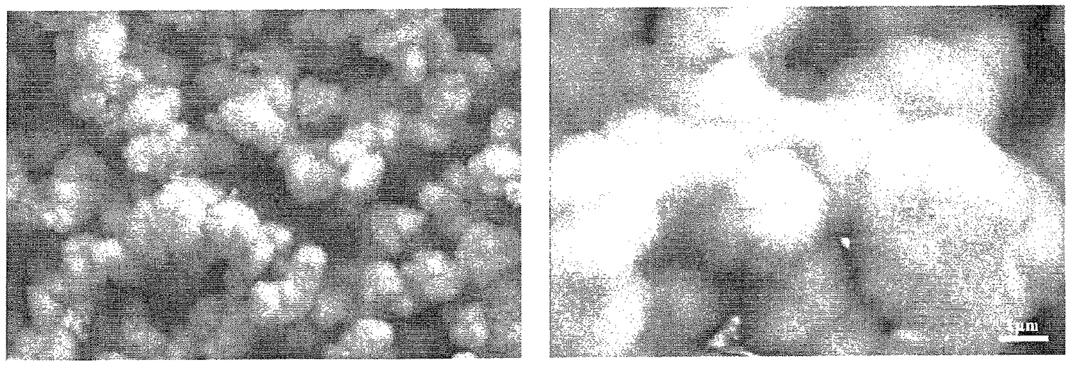
FIG. 1 illustrates the morphology of SrCaP after treated at 60° C. for 1 week using 0.06 mM Sr doped PBS.

In the present application the word “doped” is used interchangeably with “substituted”.

For the purpose of the application, biomaterials are materials intended to interface with biological systems to evaluate, treat, augment, or replace any tissue, organ or function of the body.

The chemical formula for stoichiometric hydroxyapatite (HA) is $Ca_{10}(PO_4)_6(OH)_2$, but for the purpose of this application many variations can be used. The present invention is mainly described in terms calcium phosphates (CaP) which includes but is not limited to dicalcium phosphate dihydrate (DCPD), octacalcium phosphate (OCP), tricalcium phosphate (TCP), and amorphous calcium phosphate (ACP) or any derivative thereof. Diverse ions can be incorporated in the three sub-lattices and therewith the properties of the material, as for example solubility, crystal structure, degree of crystallinity, crystal size or porosity, may be changed. Potentially, cationic substitution ions are $Sr^{2+}$, $Mg^{2+}$, $Si^{4+}$, $Zn^{2+}$, $Ba^{2+}$, $Fe^{3+}$ or $Ti^{4+?}$ and anionic substitution ions are $Cl^-$, $F^-$, $HCO_3^-$ or $CO_3^{2-}$. The source for the ion substitutions can be soluble salts and slightly-soluble salts containing the ions to be substituted, such as but not limited to $SrCl_2$, $SrCO_3$, $Sr(NO_3)_2$, $Na_2SiO_3$, calcium silicates such as ($CaOSiO_2$, $CaO(SiO_2)_2$, $CaO(SiO_2)_3$); $ZnCl_2$, $ZnSO_4$, $BaCl_2$, $FeCl_3$, $Fe(NO_3)_3$, $Na_2CO_3$, NaF, $Na_2FPO_4$ $NaHCO_3$ or $NaTiO_3$.

In a method in accordance with the invention ion substituted CaP particles with controlled morphology are prepared in a biomimetic process without surfactants. Biomimetics, a term coined by Otto Schmidt in the 1950s, means to study natural processes and to transfer the gained knowledge from biology to technology, thus, imitating the processes that occur in nature, in this case the biomineralisation.

Below is a general, non-limited, overview of the present invention and some of the various morphologies, how they are affected by different factors and how they are obtained through the present invention:

The present invention involves aggregates, preferably spherical, of smaller units of ion substituted CaP in order to control the morphology and structure The morphology of the units/crystals are affected by ion concentration Preferably the diameter of the particles is less than 1000 nm, more preferably less than 100 nm preferably the diameter is larger than 10 nm.

When using strontium as substitution ion the ratio of $Sr^{2+}$:$Ca^{2+}$:$HPO_4^{2-}$ is preferably x:1:10, wherein x is preferably $0<x\leq 0.67$ for example x is 0 or more, or more than 0.10 or more than 0.20 or more than 0.30 or 0.67 or less, or less than 0.50 or less than 0.40

0.01-0.09 mM to form an irregular spherical porous particle with a diameter of 700 nm-2 μm 0.01-0.1 mM to form a spherical porous particle with a diameter of about 100-300 nm 0.2-0.4 mM to form regular spherical particles with a hollow core and a porous shell, and with a diameter of about 200-500 nm 0.5-0.7 mM to form spherical particles with a dense shell and a porous core and with a diameter of 100-500 nm.

Figure 9:
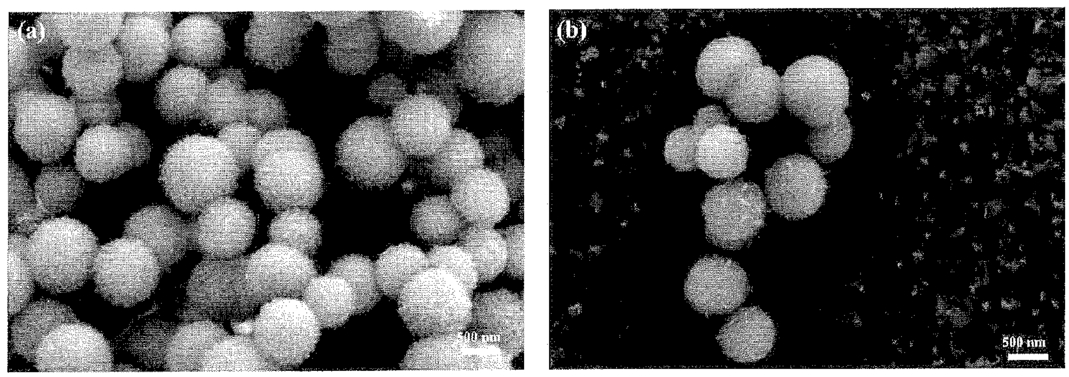
FIG. 9 illustrates the morphology of FCaP after hydrothermalized at 100° C. using (a) 0.04 mM and (b) 0.2 mM F doped PBS for 24 hours.

FIG. 9' shows the porous morphology of calcium phosphate aged at 60° C. for 1 week with increasing strontium concentration from 0 to 0.6 mM in (A) to (E). The Ca/P ratio is 0.1. Arrows in (D) indicate the hollow nature of the particles. Also FIGS. 10', 11 and 12 illustrates strontium doped CaP.

When using fluoride as substitution ion the ratio of $F^-$:$Ca^{2+}$:$HPO_4^{2-}$ is preferably x:1:10, wherein x is preferably $0<x\leq 0.22$, for example x is more than 0.05 or more than 0.10 or 0.22 or less or less than 0.15 to form spherical porous particles with a diameter of about 300-500 nm

When using silicon as substitution ion the ratio of $SiO_3^{2-}$:$Ca^{2+}$:$HPO_4^{2-}$ could be x:1:10, preferably with $0<x\leq 10$, for example 1, 2, 3, 4, 5, 6, 7, 8, 9 or 10, to form spherical porous particles with a diameter of about 200-500 nm.

In the following examples the formation of ion substituted CaP particles with different morphology will be described in more detail. Since many of the exemplified processes aim at a spherical shape of the CaP particles the particles are interchangeably referred to as nanospheres.

Example 1

Strontium substituted porous CaP nanospheres were synthesized from a Sr-doped supersaturated phosphate buffer solution containing $Ca^{2+}$, $HPO_4^{2-}$, $Na^+$, $K^+$, $Cl^-$, $Mg^{2+}$ (for concentrations see Table 1) in a static process. To mimick a body fluid, the pH value of Sr doped phosphate buffered saline was controlled at 7.4. The starting ratio of $Sr^{2+}$:$Ca^{2+}$:$HPO_4^{2-}$ was x:1:10 (wherein x is 0 to 0.67). Strontium substituted CaP crystallized, grew and self-assembled in the supersaturated solution. In order to increase the progress of crystal growth and self assembly, the treatment was performed at 37° C. or 60° C. in an oven during a static process.

The process resulted in Sr-substituted CaP nanospheres with an outer shell structure and porous inner and a particle size of about 100-1000 nm.

Figure 2:
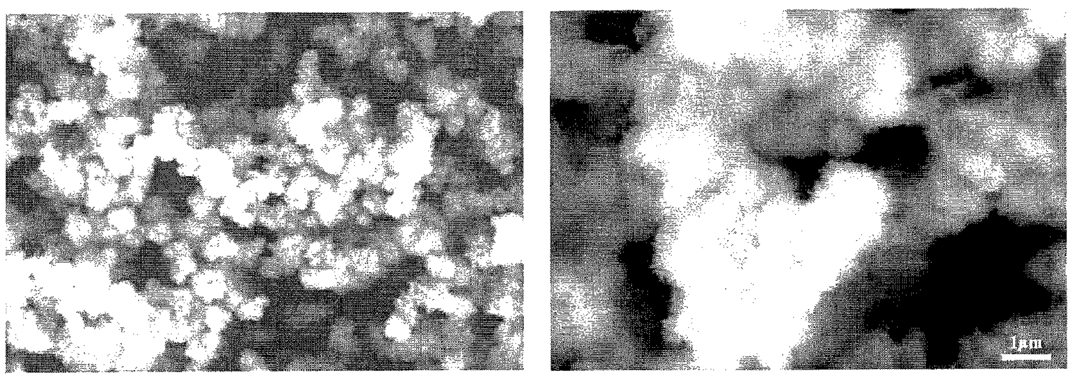
FIG. 2 illustrates the morphology of SrCaP after treated at 60° C. for 1 week using 0.15 mM Sr doped PBS.
Figure 3:
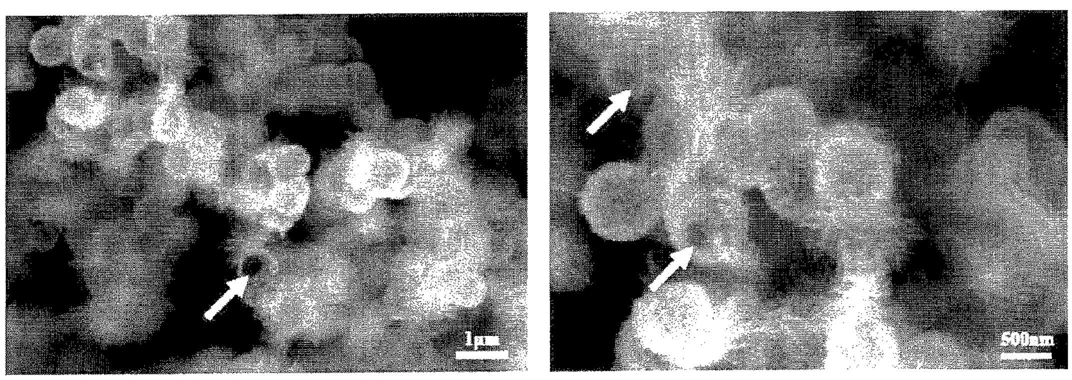
FIG. 3 illustrates the morphology of SrCaP after treated at 60° C. for 1 week using 0.3 mM Sr doped PBS. The arrows in the figure illustrate hollow particles.
Figure 4:
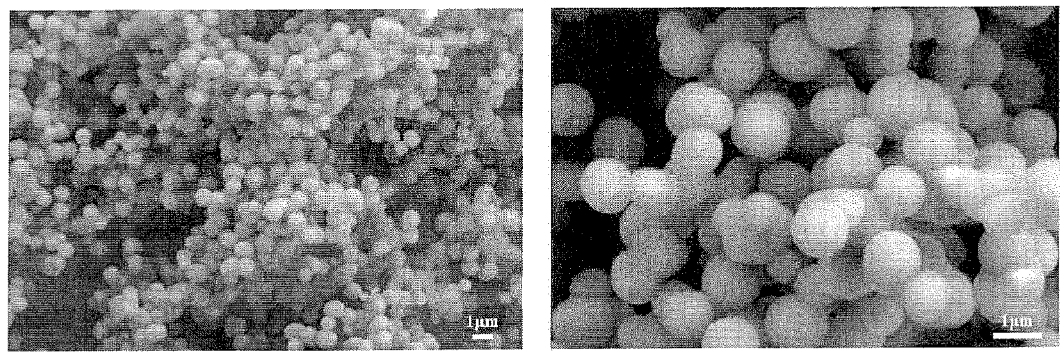
FIG. 4 illustrates the morphology of SrCaP after treated at 60° C. for 1 week using 0.6 mM Sr doped PBS.
Figure 5:
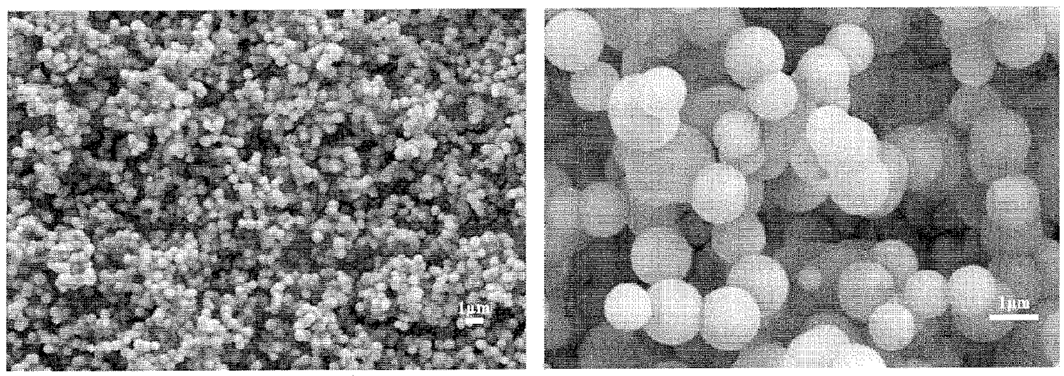
FIG. 5 illustrates the morphology of SrCaP after treated at 60° C. for 2 weeks using 0.6 mM Sr doped PBS.
Figure 6:
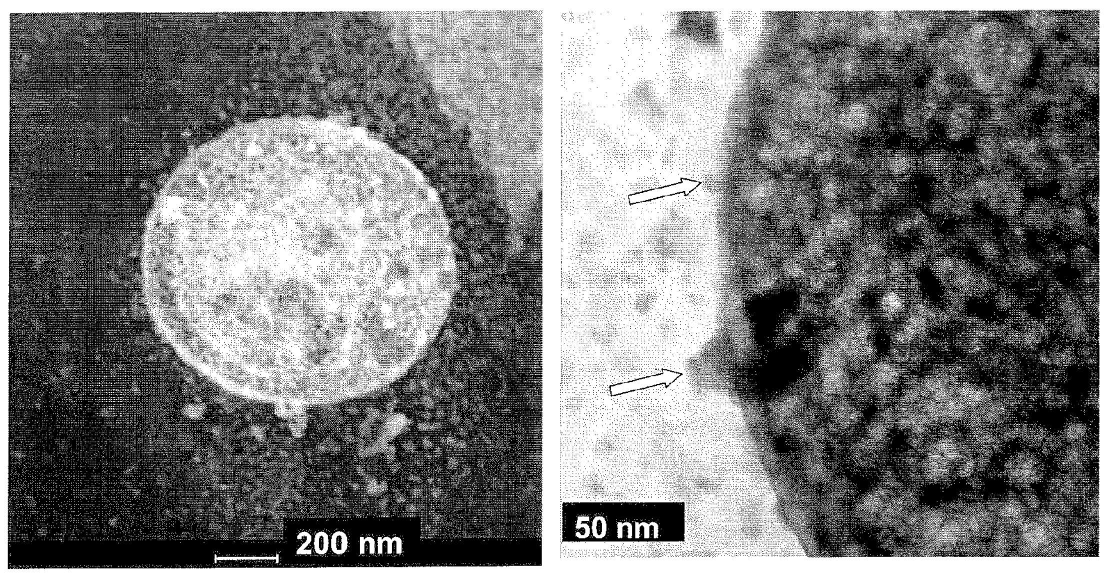
FIG. 6 illustrates TEM images of SrCaP particles which were obtained by using 0.6 mM Sr doped PBS at 60° C. for 1 week.

The morphologies of Sr-substituted CaP nanospheres were changed with the strontium ion concentration in the phosphate buffer solution. When the starting concentration of Sr in the PBS solution is 0.06 mM, the nanospheres became irregular spherical porous particle with a diameter of about 1 micrometer (FIG. 1). When the starting concentration of Sr PBS solution is increased to 0.15 mM, the size of spheres decreases to 100-300 nm and the particles became spherical with a hollow core and a porous shell (FIG. 2). When Sr ion concentration was increased to 0.3 mM, the particles became regular spheres with a hollow core and a porous shell, and with a diameter of about 200-500 nm (FIG. 3). However, after the starting concentration of Sr PBS solution was increased to 0.6 mM, the particles turned into spheres with a dense shell and a porous core, and with a diameter of about 100-500 nm (FIG. 4, FIG. 6). When the treating time was increased to 2 weeks, the morphology did not change, and the particles did not grow and the size became the same as that of the results of 1 week (FIG. 5).

Example 2

The same experimental procedure as in example 1 but the solution was magnetically stirred in a water bath at 37° C. or 60° C.

The process resulted in Sr-substituted CaP nanospheres with a hollow core and a shell which was rougher than that of the static process, and with a particle size of about 200-400 nm.

Figure 7:
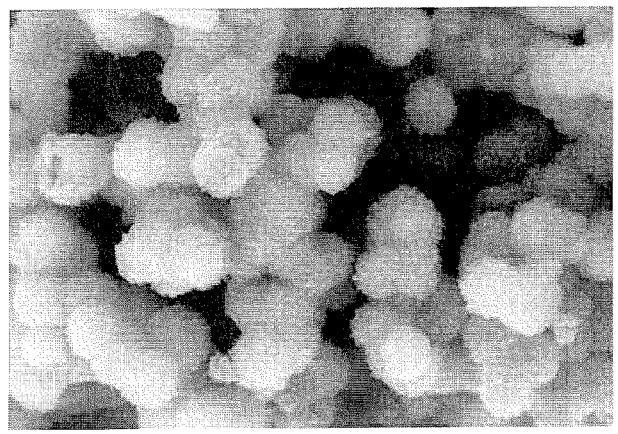
FIG. 7 illustrates the morphology of SrCaP after stirred at 60° C. using 0.6 mM Sr doped PBS for 1 day.

In FIG. 7 the morphologies, spheres with rough outer layer and hollow core of such Sr-substituted CaP nanospheres are illustrated. The reaction was stirred for 1 day at 60° C. in a 0.6 mM Sr doped PBS.

Example 3

The same experimental procedure as in example 1 but the solution was put into an autoclave at 60° C., 80° C. or 100° C. to obtain a hydrothermal process.

The process resulted in Sr-substituted CaP nanospheres with a dense shell and a porous inner and a particle size of about 200-500 nm. Via a hydrothermal process, the synthesis time was greatly shortened from 1 week to 1 hour.

Figure 8:
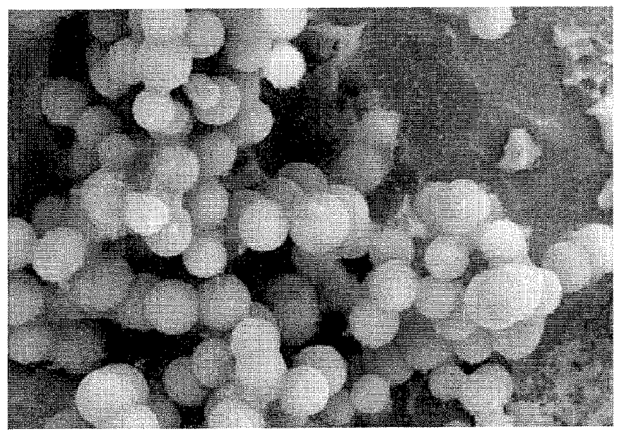
FIG. 8 illustrates the morphology of SrCaP after hydrothermalized at 100° C. using 0.6 mM Sr doped PBS for 1 hour.

In FIG. 8 the morphologies, spheres with smooth surface, of such Sr-substituted CaP nanospheres are illustrated. The reaction was hydrothermalized for 1 hour at 100° C. in a 0.6 mM Sr doped PBS.

Accordingly examples 1 to 3 and the corresponding FIGS. 1 to 8 show that the Sr ion concentration in the phosphate buffer solution can be used to control the morphology of Sr-substituted particles. An effect of Sr concentration on the morphology of hydroxyapatite nanocrystals has previously been observed by Bigi et al., Inorganica Chemica Acta 2007; 360:1009-1016. In their study the morphology of Sr-substituted nanocrystals change from plate-shaped to more perturbed shaped with ill-defined edges when reducing the Sr-content. Previous studies have not show any production of spheres or spherical particles and they did not present any results on how the concentration affects the morphology. At higher Sr-content the crystal dimensions increase with increasing Sr-content. These larger nanocrystals, i.e. 0.5×0.1 μm, have very well-defined shape elongated in a direction parallel to the crystallographic c-axis. In contrast the Sr-substituted particles of the present invention are substantially spherical aggregates, referred to as nanospheres and microspheres of 10-1000 nm, of a multitude of nanocrystals. Moreover, in addition to change of morphology when changing the Sr ion concentration the size of the nanospheres decrease when the Sr ion concentration is increased. Examples 1 to 3 resulted in four characteristic morphologies, as shown in: FIG. 1, an irregular spherical porous particle with a diameter of about 1 μm; FIG. 2, a spherical particle with a hollow core and a porous shell and a diameter of about 100-300 nm; FIG. 3, a regular spherical particle with a hollow core and a porous shell and a diameter of about 200-500 nm; and FIGS. 4-6, spherical particles with a dense shell and a porous core and a diameter of about 100-500 nm.

The present invention is not limited to control of the morphology by means of Sr concentration. The following examples demonstrate control of the morphology of particles formed using fluoride substitution and silicon substitution the latter could be exemplified with silicates such as silica. These examples show that by choosing different substitution ions or combining different substitution ions and by altering the substitution ion concentrations a wide range of shapes, sizes and morphologies can be obtained.

Example 4

Fluoride substituted porous CaP nanospheres were synthesized from an F-doped supersaturated phosphate solution containing $Ca^{2+}$, $HPO_4^{2-}$, $Na^+$, $K^+$, $Cl^-$, $Mg^{2+}$ in a hydrothermal process. To mimick a body fluid, the pH value of F doped phosphate buffered saline was controlled at 7.4. The starting ratio of $F^{-:Ca2+}$:$HPO_4^{2-}$ was x:1:10 (wherein x is 0 to 0.22). Fluoride substituted calcium phosphate crystallized, grew and self-assembled in the supersaturated solution. The synthesis was a hydrothermalization process performed at 60° C., 80° C. or 100° C. in an oven.

The process resulted in spherical porous F-substituted particles with a diameter of about 300-500 nm.

In FIG. 9 the morphology of such F-substituted CaP particles after being hydrothermalized at 100° C. using 0.04 mM (FIGS. 9*a*) and 0.2 mM (FIG. 9*b*) F doped PBS for 24 hours is illustrated. When compared with the images of the Sr-substituted particles in e.g. FIGS. 4-6 it can be appreciated that the morphology of the surface of the F-substituted particles differs from the surface morphology of the Sr-substituted particles, i.e. the Sr-substituted particles have a smoother surface than the F-substituted particles that have a rough surface with sheets protruding from the surface.

One effect on the crystal morphology of fluoride-substituted apatites has been shown in Jha et al, Journal of Materials Science: Materials in Medicine 1997; 8:185-191). In their work spheroidal or more acicular crystals were precipitated. It was found that lowering of the precipitation temperature and increasing of fluoride ion concentration tended to reduce the aspect ratio of the crystallites produced. In the present invention the fluoride concentration is used to obtain spherical aggregates of fluoride-substituted calcium phosphate crystals where the aggregates have a controlled morphology. In many of the above mentioned applications control of the morphology of the aggregates is of outmost importance, whereas the morphology of the crystals has limited effect.

Example 5

Silicate substituted porous calcium phosphate nanospheres were synthesized from an Si-doped supersaturated phosphate solution containing $Ca^{2+}$, $HPO_4^{2-}$, $Na^+$, $K^+$, $Cl^-$, $Mg^{2+}$. To mimick a body fluid, the pH value of silicate doped phosphate buffered saline was controlled at 7.4. The starting ratio of $SiO_3^{2-}$:$Ca^{2+}$:$HPO_4^{2-}$ was x:1:10 (wherein x is 0 to 10). Calcium phosphate with silicate substitution crystallized, grew and self-assembled in the supersaturated solution. In order to increase the progress of crystals' growth and self assembly, the solution was put into an autoclave at 80° C. or 100° C.

The process resulted in spherical porous Si-substituted CaP particles with a diameter of about 200-500 nm.

Figure 10:
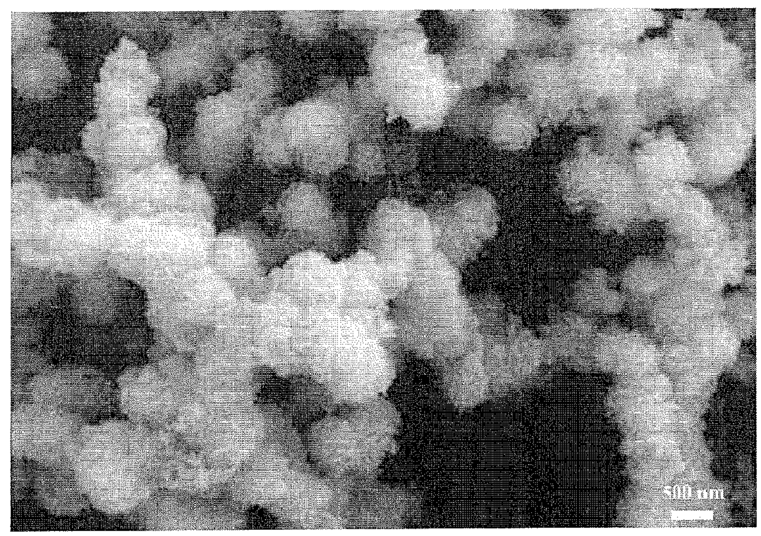
FIG. 10 illustrates the morphology of SiCaP after hydrothermalized at 100° C. using 6 mM Si doped PBS for 24 hours.

In FIG. 10 the morphology of such Si-substituted CaP particles after being hydrothermalized at 100° C. using 6 mM Si doped PBS for 24 hours is illustrated. Like the F-substituted particles of FIG. 9 the surface of the Si-substituted particles of FIG. 10 is comparatively rough and comprises flakes protruding from the surface. However, the F-substituted particles have a more regular spherical shape.

Example 6

Porous calcium phosphate nanospheres were synthesized from a supersaturated phosphate solution containing $Ca^{2+}$, $HPO_4^{2-}$, $Na^+$, $K^+$, $Cl^-$, $Mg^{2+}$ (for concentrations see Table 1). For mimicking a body fluid sounding, the pH value of this phosphate buffered saline was controlled at 7.4 before next treatment. The starting ratio of $Ca^{2+}$:$HPO_4^{2-}$ was 1:10. Calcium phosphate crystallized, grew and self-assembled from the supersaturated solution. In order to increase the progress of crystals' growth and self assembly, the solution was put into an autoclave at 80° C. or 100° C.

The process resulted in porous particles with a diameter of about 300-500 nm.

Figure 11:
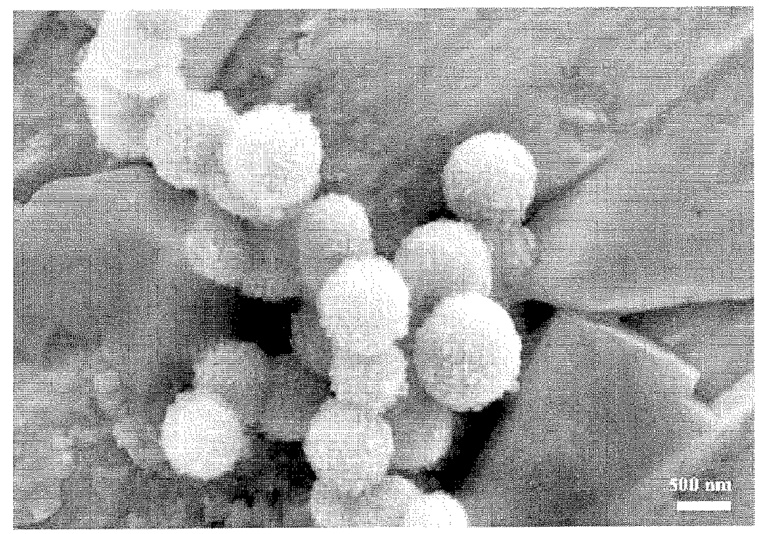
FIG. 11 illustrates the morphology of CaP after aged at 100° C. using pure PBS for 24 hours, FIG. 9' shows Sr-doped CaP particles with increasing Ca/P ratios in accordance with the invention, FIG. 10' shows F-doped and Si-doped particles in accordance with the invention, FIG. 1' (*a*)-(*c*) shows morphology obtained using M1, M2 and M3-Sr, respectively, in accordance with the present invention, FIG. 2' (*a*)-(*d*) shows morphology of particles from M2-H2O (without buffer solution) in accordance with the invention, FIG. 3' shows influence of Mg and Sr on the morphology of the particles fabricated using M2, FIG. 4' shows an XRD-pattern of the particles fabricated using M2 of different Mg and Sr concentrations in accordance with the invention, FIG. 5' shows morphology of particles fabricated using M3 in accordance with the invention, FIG. 6' shows XRD-pattern of particles fabricated using M3-Sr in accordance with the invention, FIG. 7' shows cumulative strontium release of 100 mg particles fabricated using M1 in accordance with the invention, and FIG. 8' shows morphology of the particles from M1 after 13 days ageing in aqueous solutions at 37° C. in accordance with the invention.
Figure 1:
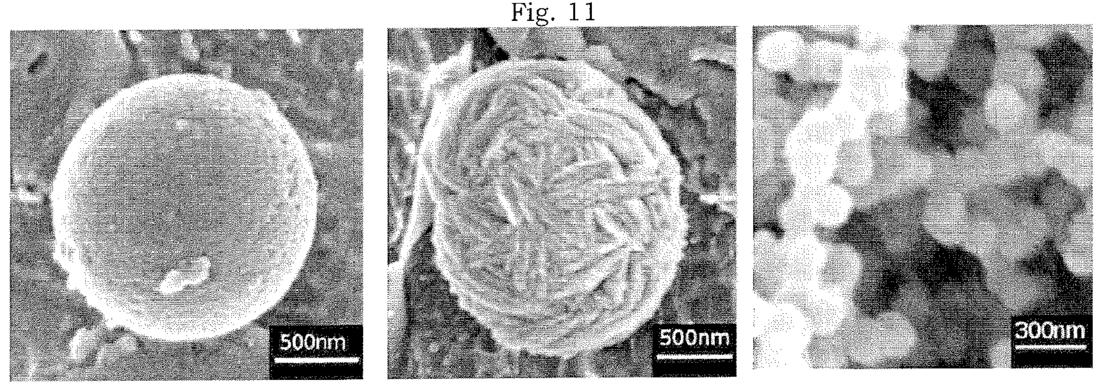
Figure 2:
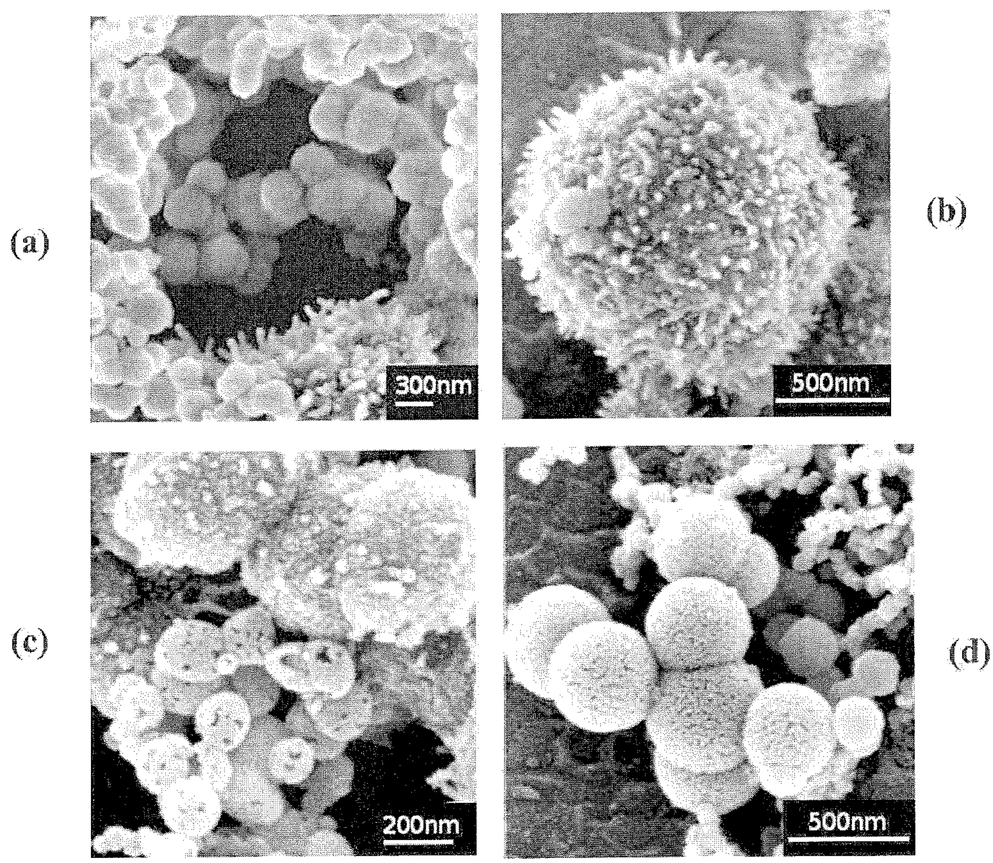
Figure 3:
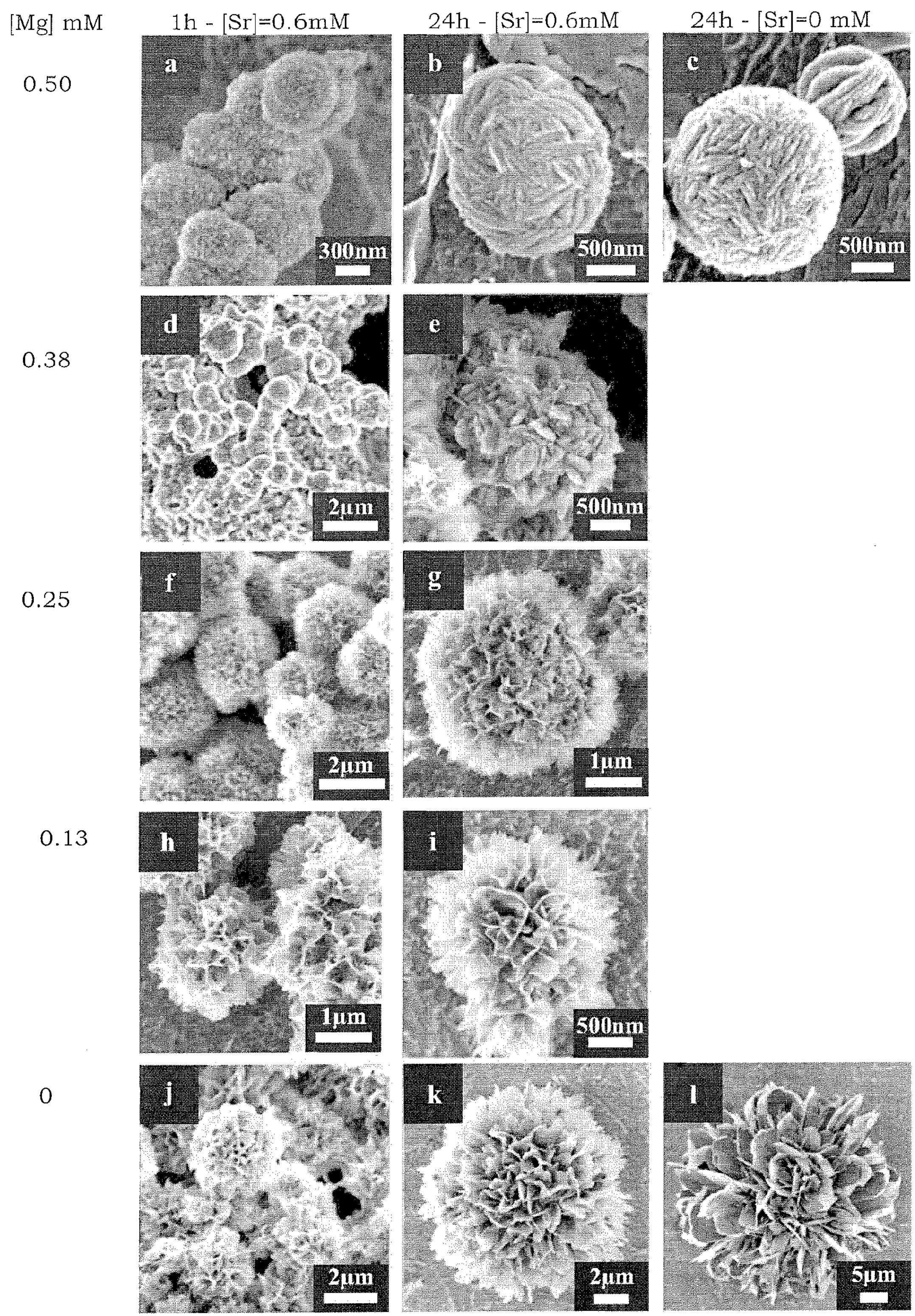
Figure 4:
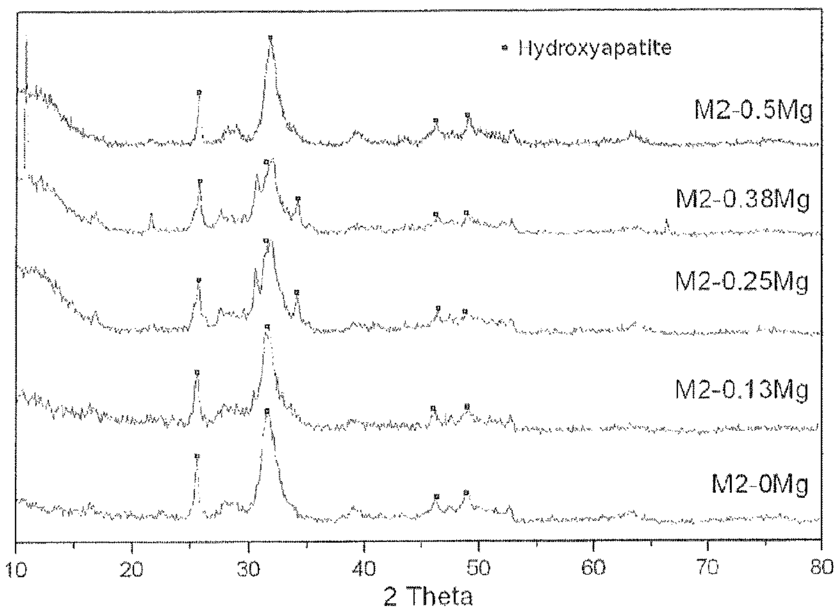
Figure 5:
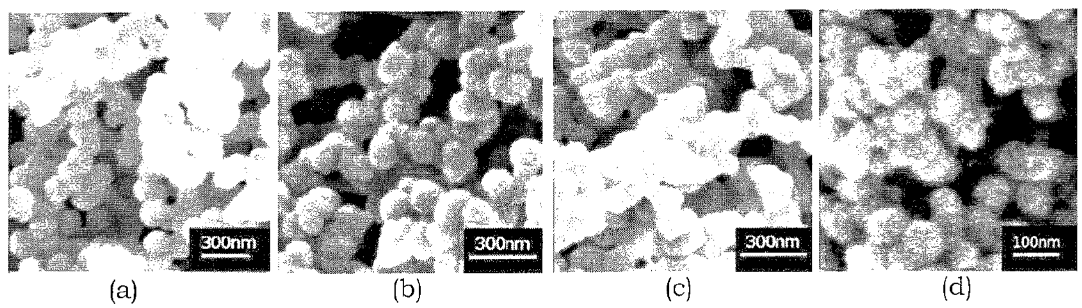
Figure 6:
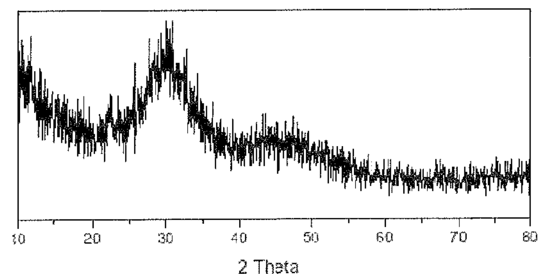
Figure 7:
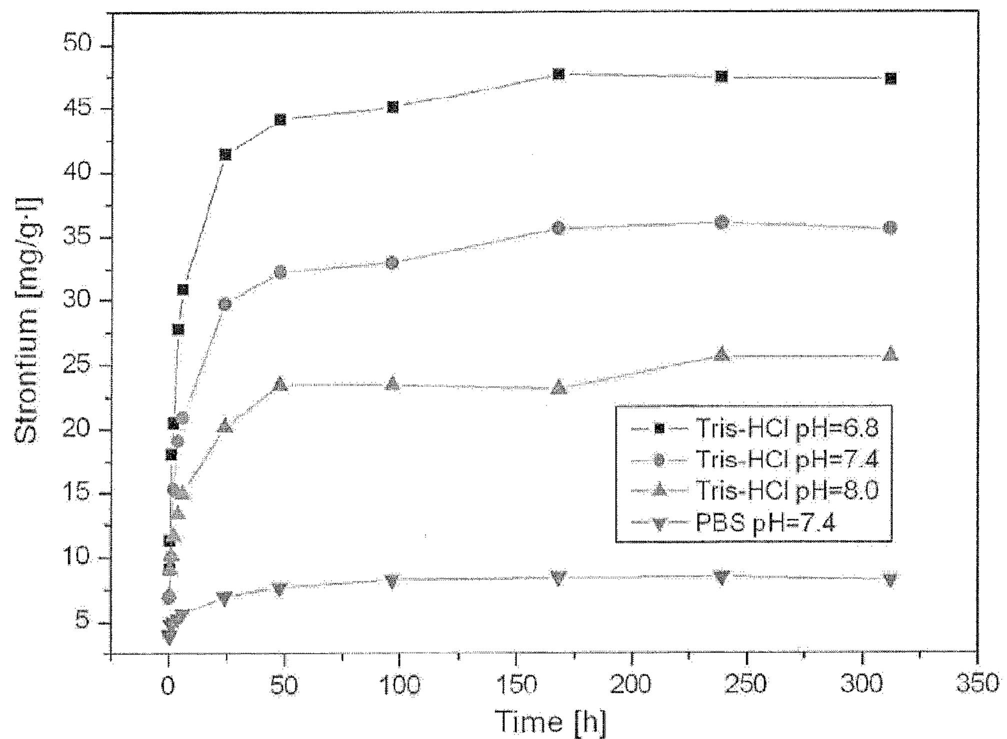
Figure 8:
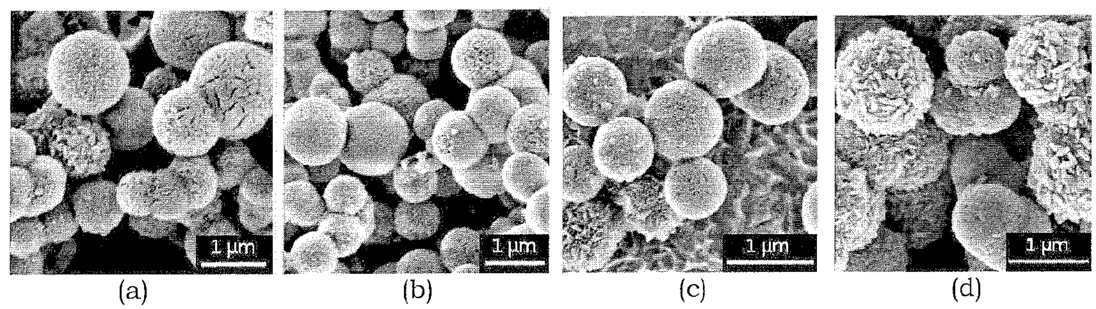
Figure 9:
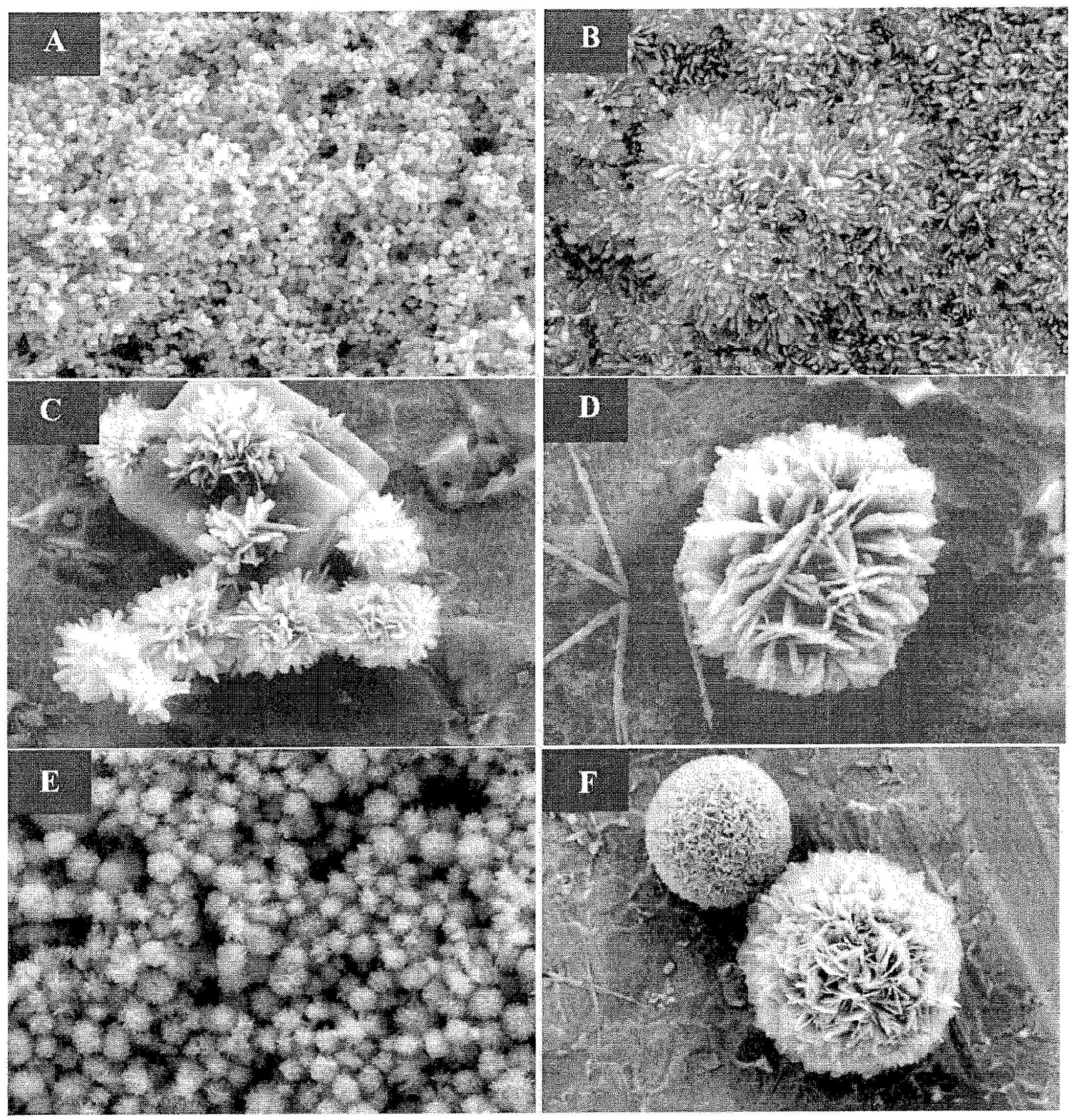
Figure 10:
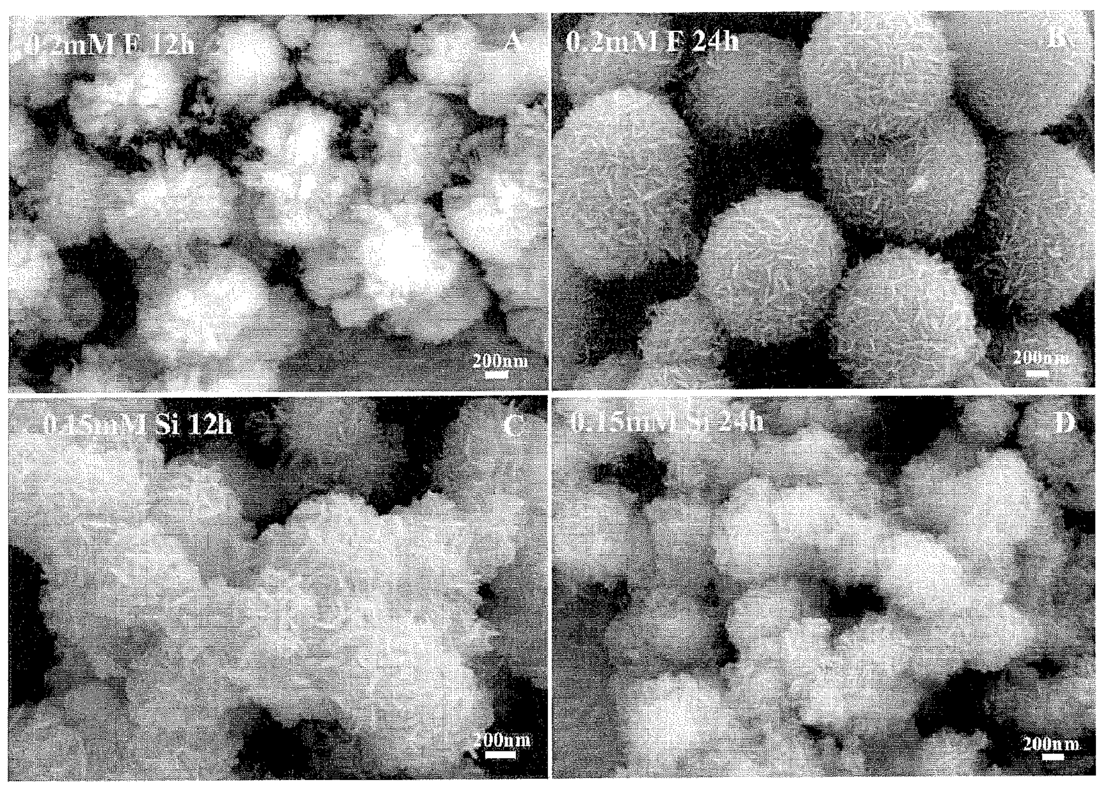
Figure 11:
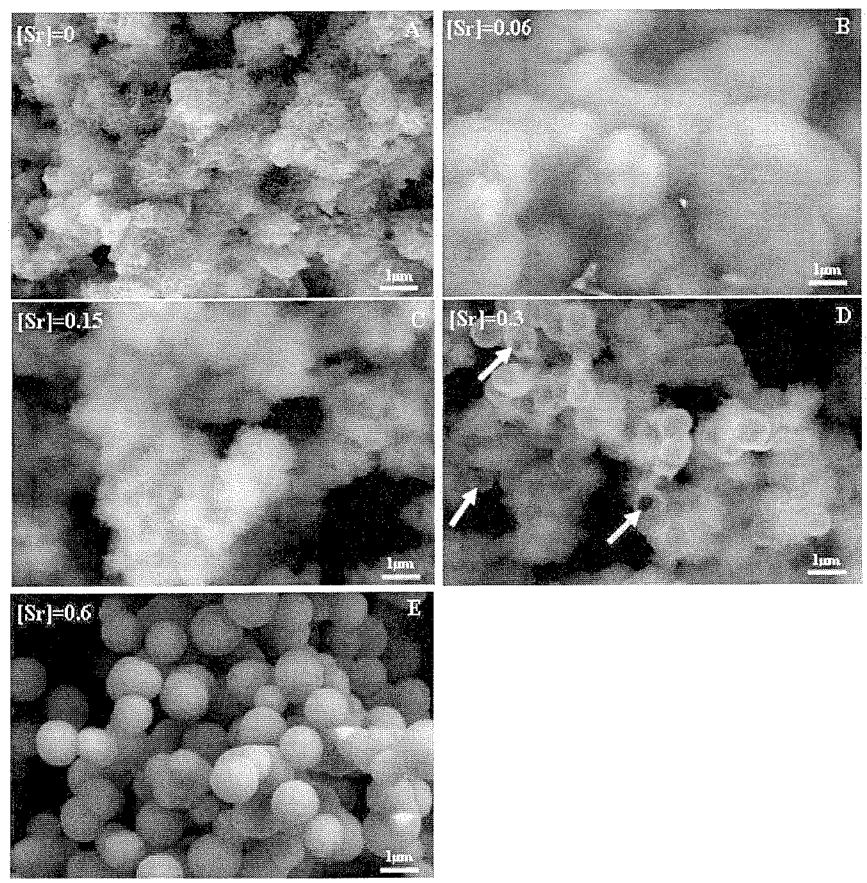
Figure 12:
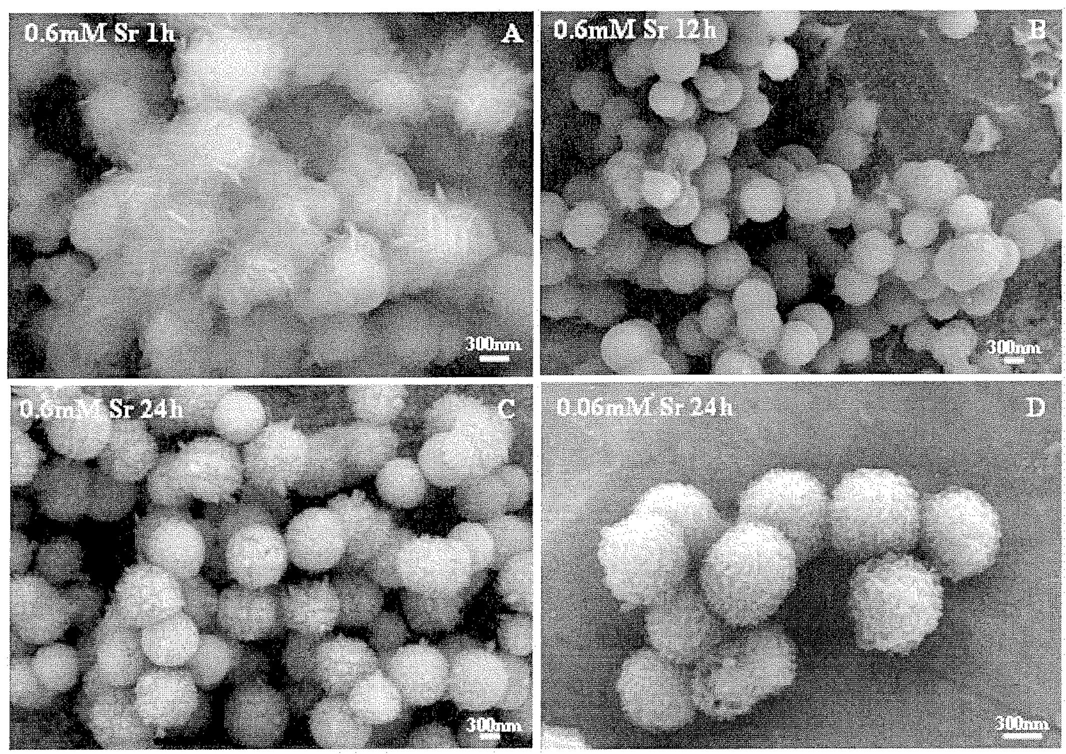
FIG. 12 shows SEM images of strontium-doped calcium phosphate spheres treated at 100° C. for varying reaction times.
Figure 13:
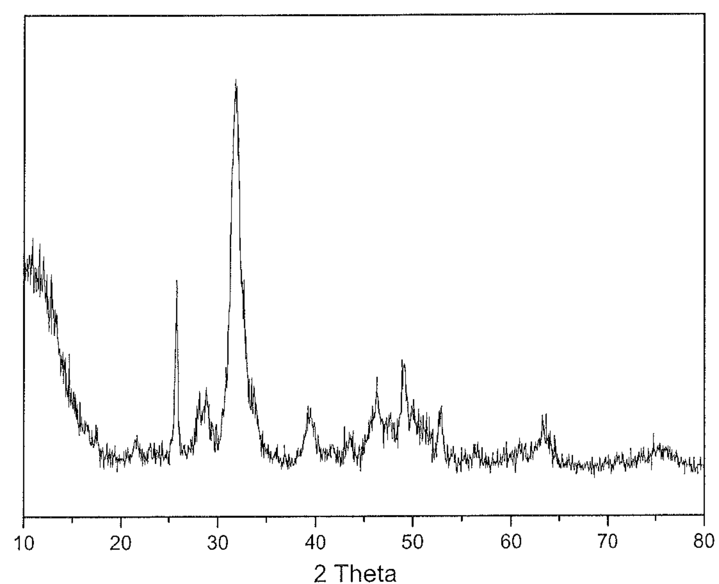
FIG. 13 shows XRD pattern for Sr—CaP spherical particles using the solution with 0.6 mM of Sr ion.

In FIG. 11 it is illustrated the morphology of such particles after being hydrothermalized at 100° C. using pure PBS for 24 hours.

Example 7

In another example the Ca/P ratio of the buffer solution is varied from 0.1 to 1.0 mM calcium and 10 mM phosphate ions, while the Sr is varied from 0-0.6 mM, and the particles are aged at 60° C. for 1 week. The calcium phosphate particles precipitate as random clusters of nano-flakes in absence of strontium ions. After strontium addition to the phosphate buffered saline, a change in particle morphology is noted. With an increase in Sr concentration to 0.06 mM, the flake-like CaP particles aggregate much more regularly than that obtained from the solution without strontium ions. A further Sr-ion increase to 0.15 mM results in particle aggregation into spheres with a much smaller diameter. The individual CaP particles still assemble with flake-like nano-calcium phosphate. The morphology of CaP particles after Sr increase to 0.3 mM is spherical with flake-like wings surrounding the spheres. The average diameter of these CaP particles is approximately 500 nm. It is particularly interesting that these CaP spheres are hollow. When the concentration of Sr ion increases to 0.6 mM, the CaP particles appear completely spherical, and the diameter is 200 nm-1 μm. XRD analysis of this sample presents specific peaks of calcium phosphate with (002), (211), and (203) confirming that these spheres are calcium phosphate crystals.

The structure of CaP particles obtained from 0.6 mM strontium solution has been further analyzed by high-angle annular dark-field (CaPADF) scanning transmission electron microscope (STEM). It is clear that the CaP sphere has a hollow core and a shell of approximately 100 nm in thickness, FIG. 6. Elemental maps from EDXS confirm that the spheres contain Ca, P, O, and Sr and a homogenous distribution throughout the samples. The elemental maps also confirm that the spheres are indeed hollow because the Ca, P, O, and Sr signals just distribute along the shell.

It is clear that the addition of strontium ions is a key factor in changing not only the composition, but also the morphology and structure of calcium phosphate in this mineralization process. The morphology of calcium phosphate varies from the random clusters of flake-like particles, to regular clusters of flake-like particles, to spherical particles with a rough surface, to hollow spheres with a rough shell, and finally, to hollow spheres with a smooth shell. This phenomenon facilitates the possibility to alter the morphology and structure of the CaP with the use of only an inorganic ion, as opposed to a structure directing surfactant. The present invention provides a strategy that ensures that the final material is doped CaP, and no other residuals or other crystals, such as strontium phosphate.

The morphology of strontium-doped calcium phosphate is not only dependent on Sr ion concentration but also influenced by the calcium to phosphate ratios. In this system, the higher the Sr concentration and calcium to phosphate ratio, the more spherical the shape becomes.

By way of example, for a strontium concentration of 0.6 mM CaP particles with a diameter of 20-40 nm were obtained when the Ca/P ratio was 0.1, whereas when increasing the Ca/P ratio to 1.0 the CaP grows into nano-flakes with a tendency to aggregate together with a flower-like morphology. When the Ca/P ratio further increases to 2.5, the flake-like particles self-assembled into spherical particles with the diameter of 0.6-1 μm. Furthermore, when the Ca/P ratio increases to 5.0, the CaP particles show a well-formed spherical morphology with a porous structure and increase in diameter to approximately 1-5 μm. FIG. 9' shows ion-doped CaP particles with increasing ratio: (A) 0.1, (B) 1.0, (C) and (D) 2.5, (E) and (F) 5.0.

The temperature of the solution treatment also has large effect on the morphology of the resultant particles. A solution containing 1.0 mM calcium ions, 10 mM phosphate ions, and 0.6 mM of strontium ions produced well-formed hollow CaP spheres after 1 week when treated at 60° C. When increasing the temperature to 100° C. spherical CaP nanoparticles are formed after 1 hour treatment. These particles have a diameter of 200-500 nm and are covered with nano-flakes. After a 12 hour reaction, the CaP spheres appear much smoother, and the diameter of spheres increases to 500-800 nm. The diameter of CaP spheres further increase to 600 nm-1 μm after a 24 hour reaction and the surface becomes rougher than that obtained after a 12 hour reaction. Long and flake-like particles grow radially from the inner part of CaP spheres. CaP spheres prepared from a $Sr^{2+}$ concentration of 0.06 mM do not produce CaP spheres under 60° C. but with an increase in temperature to 100° C., spherical particles are easily formed.

In addition to strontium, other ions may be added to the phosphate buffer solution, such as fluoride, and silicate ions for example $SiO_3^{2-}$, as shown in the above examples, which, similarly to Sr, are natural substitutions in bone mineral.

Fluoride and silicon doped CaP (F—CaP and Si—CaP) particles with controlled morphology are formed after adding these ions to the phosphate buffer solution and treating at 100° C. for 12 and 24 hours. F-CaP particles form spheres after just 12 h (FIG. 6A). Needle-like particles grow radially from the spherical inner core to create well-formed spheres. After treating for 24 hours, the fluoride doped CaP particles become spherical. However, the silicon doped CaP particles appear spherical. The reaction temperature plays a key role in spherical particle formation in the Si/F—CaP system, preferably the temperature should be above 60° C. FIG. 10' shows SEM images of calcium phosphate spheres prepared from a phosphate buffer solution treated at 100° C. containing 0.2 mM fluoride ion for (A) 12 hours and (B) 24 hours, and 0.15 mM silicate ion for (C) 12 hours and (D) 24 hours.

The effect of increasing the reaction temperature in a static process is similar to that of a hydrothermal method. High temperature not only increases the formation rate of strontium doped CaP spheres, but also enables preparation of fluoride and silicon doped CaP spheres, which cannot be prepared at low temperature.

As stated earlier that no additional heat treatment is necessary, particles fabricated using the method according to the invention may as well be heat-treated to change the morphology of the crystals or the degree of crystallinity. Options for this are calcining in an oven at high temperature or ripening in an aqueous media.

Example 8

A toothpaste containing spherical Sr-substituted CaP particles manufactured according to example 1 with 0.15 mM Sr solution, the size of spheres was 100-300 nm and the particles was spherical with a hollow core and a porous shell. 7 wt. % of CaP particles was added to a commercial available toothpaste (ACTA, Cederbloms, Väsby Sweden). The purpose of this study was to evaluate the occlusion of dentin tubules with CaP particles.

Method: In vitro experiments were performed using standardized slabs of human dentin from extracted teeth. Discs were cut from extracted teeth and prepared by grinding and polishing to standardize the test surfaces. They were etched to remove any smear layer to allow for good observation, and the slabs were cut in half to provide matching test and control samples. The polished surface of the dentin block was gently swabbed in a circular motion with its respective treatment for 30 seconds. The treatment material was allowed to sit on the dentin block for 30 more seconds and then rinsed vigorously with tap water for approximately 60 seconds to remove toothpaste residue. The samples were then dried and placed in a 37° C. simulated saliva bath for 5 minutes. After 5 minutes the samples were treated again, following the same process until each sample had been treated for a total of 10 times. All samples were mounted for scanning electron microscopy (SEM) for visualisation of effect.

Results: Under SEM evaluation it was noted that the control samples had abundant open dentin tubules, but the treated samples had very few open tubules. The tubules were occluded both by remaining CaP particles Example 9

In the following the formation of ion substituted CaP particles for controlled morphology and controlled ion release, such as strontium release, from the prepared particles in human body or body simulated environment will be described in detail with reference to three different approaches utilizing 1) salt solutions based on Dulbeccos's phosphate buffer solution D8862 (D-PBS), 2) self-made Tris-HCl and 3) distilled water, hereinafter referred to as M1, M2 and M3, respectively. Examples of these salt solutions are found in Table 1. The concentrations of one or more of the constituents of the salt solutions can be varied.

TABLE 1

| | Ca/P | Sr 2+ (mM) | Other (mM) | Comment |
|---|---|---|---|---|
| D-PBS | | | | |
| M1 | 0.1 | 0.6 | 0.5 $Mg^{2+}$ | 100° C., 24 h |
| Tris-HCl | | | | |
| M2 | 0.1 | 0.6 | 0.5 $Mg^{2+}$ | 100° C., 1 h/24 h |
| M2-0.38Mg | 0.1 | 0.6 | 0.38 $Mg^{2+}$ | 75% [$Mg^{2+}$] |

TABLE 1-continued

| | Ca/P | Sr 2+ (mM) | Other (mM) | Comment |
|---|---|---|---|---|
| M2-0.25Mg | 0.1 | 0.6 | 0.25 $Mg^{2+}$ | 50% $[Mg^{2+}]$ |
| M2-0.13Mg | 0.1 | 0.6 | 0.13 $Mg^{2+}$ | 25% $[Mg^{2+}]$ |
| M2-0Mg | 0.1 | 0.6 | 0 | without $Mg^{2+}$ |
| M2-0Sr | 0.1 | 0 | 0.5 $Mg^{2+}$ | without $Sr^{2+}$ |
| M2-0Mg—0Sr | 0.1 | 0 | 0 | without $Mg^{2+}$ and $Sr^{2+}$ |
| M2-H2O Distilled water | 0.1 | 0.6 | 0.5 $Mg^{2+}$ | in distilled Water |
| M3 | 2.4 | 0 | 29.4 $HCO^{-3}$ | room temperature, 5 min/1 h |
| M3-Sr | 2.4 | 0.6 | 29.4 $HCO^{-3}$ | with $Sr^{2+}$ |
| M3-Sr-2x | 2.4 | 1.2 | 58.8 $HCO^{-3}$ | double M3-Sr |
| M3-Sr-5x | 2.4 | 3.0 | 147.0 $HCO^{-3}$ | fivefold M3-Sr |
| M3-Sr—0HCO$^3$ | 2.4 | 0.6 | 0 | without $HCO^{-3}$ |

For medical applications it is necessary to know and to control the rate and the amount of the released ions and for this reason release studies are commonly performed. Therefore the CaP particles of the invention has been evaluated with respect to release of substituted ions, in particular Sr ions. To imitate body conditions, in vitro release tests are often performed in simulated body fluids, which are solutions with compositions similar those of human blood plasma and a pH-value around 7.4. Various solutions are known, some just contain the inorganic components, other try to imitate the organic substances as well.

Such release-studies, where the strontium concentration in the liquid is measured over the time, has previously been done for different types of biomaterials as for example bioglass, bone cement or multi-layered nanoparticles and two different methods are common. With the continuous mode, the cumulative release is determined and the material remains the whole time in the same liquid, whereas in the dynamic mode the liquid is changed after every sampling, thus the initial composition of the liquid is each time the same and just the released amount between two samplings is measured. To get information about the effective, respectively toxic concentrations of the released ions, cell studies need to be done, which can be performed in vitro or in vivo.

In M1 one litre D-PBS and 0.6 mM strontium nitrate (Sr $(NO_3)_2$) was filled into glass-vessels, which were tightly sealed and laid in an oven for 24 hours at 100° C. The liquid precursor can also be based on simulated body fluids (SBF). The composition of D-PBS and SBF are compared to the composition of blood plasma in the following table.

TABLE 2

| | $Na^+$ | $K^+$ | $Mg^{2+}$ | $Ca^{2+}$ | $Cl^-$ | $HCO^{-3}$ | $HPO_4^{2-}$ | $SO_4^{2-}$ | pH |
|---|---|---|---|---|---|---|---|---|---|
| Blood Plasma | 142.0 | 5.0 | 1.5 | 2.5 | 103.0 | 27.0 | 1.0 | 0.5 | 7.2-7.4 |
| SBF | 142.0 | 5.0 | 1.5 | 2.5 | 148.8 | 4.2 | 1.0 | — | 7.4 |
| D-PBS 8662 | 153.1 | 4.2 | 0.5 | 0.9 | 142.4 | — | 8.1 | — | 7.4 |

M2 is based on a self-made PBS, called Tris-HCl. One litre of this solution was prepared with 500 ml 0.1 M tris(hydroxymethyl)aminomethane (Tris), 420 ml 0.1 M HCl and 5.844 g NaCl and then filled with distilled water up to one litre solution. The pH-value was adjusted to 7.4.

The basis version of M2 is an attempt to imitate D-PBS with the self-made PBS and to study the influence of the buffer solution. All the desired ions (Ca, P, Mg) were added to the Tris-HCl in the same concentration as they are in the D-PBS used in M1. 0.6 mM strontium nitrate was added to the solution, which was then filled in glass-vessels and kept for 24 h at 100° C. (compare M1).

One purpose of the study was to show the influence of magnesium on morphology. Therefore the Mg concentration in the solution was reduced in four equal steps, which were 0.75, 0.5, 0.25 and 0 times the original Mg concentration of 0.5 mM. These methods were named M2-0.38 Mg, M2-0.25 Mg, M2-0.13 Mg, M2-0 Mg, respectively. Furthermore, time dependence, respectively ageing, was investigated, thus all variations were prepared with a reaction time of 1 hour and 24 hours, alternatively.

Another purpose was to show strontium's influence on the morphology, thus the 0.5 mM Mg and the Mg-free 24-h variation was prepared without strontium (M2-0Sr, M2-0Mg-0Sr) and in M2-$H_2O$ the same ion-concentrations as in M2 were used, but distilled water was the liquid precursor, which resulted in an initial pH of 7.2-7.3. The above table shows compositions of all variations.

In M3 distilled water was used as liquid precursor. Two separately prepared solutions (P and $HCO_3$ in the first and Ca in the second one) were added in a beaker with magnetic stirrer at room temperature. A sample was taken after 5 minutes reaction time.

In M3-Sr 0.6 mM strontium was added and samples were taken after 5 minutes and 1 hour. In M3-Sr-0$HCO^{-3}$ the solution was prepared without adding carbonate and in M3-Sr-2x and M3-Sr-5x, and hence the ion concentrations were increased by factor 2 and 5 respectively, in an attempt to increase the amount of spheres per litre solution. The morphology of the prepared particles was studied with a scanning electron microscope (SEM).

X-Ray diffraction was used to determine the crystal structure of the particles. For this, a silicon wafer was covered with an ethanol-particle-solution, the ethanol was evaporated and the sample examined with a X-ray diffractometer using Cu Kα radiation (λ=1.5418). The resulting patterns were analysed by means of a computer (DIFFRACplus EVA, Bruker).

In order to benefit from the substituted ions it is necessary that the CaP particles degrade in the body. Degradation depends on many factors, as for example the pH-value, which differs between 7.35 and 7.45 for human blood, as well as from the crystallinity of the material and doping or substituting groups or ions that introduce lattice distortions into the structure of CaP. Faster degradation occurs for example through lower pH-values, incorporation of magnesium and strontium and through decreased crystallinity or increased surface area. The solubility of CaPs in general is as following: ACP>TTCP>>α-TCP>>β-TCP>>CaP, which means that amorphous calcium phosphate degrades much faster than tri-calcium phosphate and that calcium phosphate is the most stable CaP.

To demonstrate the strontium release of strontium-doped CaP particles fabricated in accordance with the invention into an immersion liquid and its dependence on the pH-value of the surrounding, four different solutions were prepared and 100 mg of the spheres from M1 were put in bottles with each 100 ml of one of these. The bottles were sealed and slightly shaken (25 rev/min in horizontal direction) at 37° C., to simulate body environment. The used solvents were Tris-HCl, whose pH-value was adjusted to 6.8, 7.4 and 8.0, respectively, thus around the pH-value of human blood, and a simple D-PBS (P4417, with P, K, Na, Cl), as well with pH-value 7.4.

12 samples were taken after reaction times between 15 min and 13 days. Every time 2 ml of the upper part of the solution in the bottle was taken out with a pipette and filled in a tube. Afterwards the bottle was refilled with 2 ml of the particular solvent. Then, the sample was centrifuged and in case that precipitation was observed, the liquid was poured in a new tube and the precipitate dispersed in 2 ml of the particular solvent. After the next sampling, the bottle was in this case refilled with this 2 ml solution instead of 2 ml fresh solvent. Additionally, 20 mg of the particle was dissolved in 5 ml 1 molar HCl to determine the overall composition of the particles.

The ion concentrations in the samples were determined with Inductively Coupled Plasma—Optical Emission Spectrometry (ICP-OES).

After 13 days ageing in the four different solutions, the particles were centrifuged, washed in ethanol and dried. A SEM was used to examine morphologic changes.

The SEM pictures in FIG. 1' show particles from the three different basic approaches, each containing strontium. All particle types exhibit a spherical shape, but each having a unique morphology. The particles from M1, shown in FIG. 1*a*', had a porous surface and diameters between 1 and 2 μm, the M2-particles, shown in FIG. 1*b*', showed a rope-like structure and were in the size of 300 nm to 2 μm and spheres produced with M3-Sr, shown in FIG. 1*c*', were only 100 to 200 nm small, and having a smooth surface structure that can not be resolved in the image. X-ray diffraction determined that the spheres from M3 were amorphous and those from M1 and M2 had a CaP crystal structure.

In the experiment M2-H2O, where the Tris-HCl buffer solution was replaced by water, the morphology of the resulting particles showed high diversity and the size distribution was wide. However, most of the particles were spherical-shaped, some were hollow, other porous or furry. A few representative examples can be seen in FIG. 2'.

In FIG. 3' the results of the experiments of M2 with varied strontium and magnesium concentrations are combined. The Mg concentration declines in vertical direction from 0.5 mM in the first row of pictures to Mg-free in the last row, whereas the first two columns show the difference between a reaction time of 1 h and 24 h and column two and three compare the particles with Sr concentration of 0.6 mM and 0 mM, respectively. It is clear that magnesium has an influence on the surface structure of the spheres. While the 24 h-particles with 0.5 mM Mg had the ball-of-wool-look (FIG. 3*b*), the Mg-free particles were highly porous and appeared flower-like (FIG. 3*k*). The border for the change of morphology is around the Mg concentration of 0.38 mM. The particle on the picture of this composition (FIG. 3*e*) shows a shape between the flower and the rope-look, but particles representing both states were represented in the sample. In the first column of FIG. 3', the state of the particles after 1 h reaction time can be seen. The nuclei of the flower-particles had already the same structure but were not yet totally spherical (FIG. 3*f, h, j*) whereas the nuclei of the 0.5 mM and 0.38 mM Mg spheres were particles with a furry surface and much smaller than the 24-hours particles (FIG. 3*a*, 3*d*). The effect of Mg was dominant and the effect of Sr was small in these experiments, but clearly the Mg-free flowers were smaller when Sr was present (FIG. 3*k*, 3*l*). In the pictures of the Mg containing spheres (FIG. 3*b*, 3*c*) no significant influence of Sr could be found.

The XRD-pattern of the particles with varied Mg concentration (reaction time 24 h) are shown in FIG. 4'. For all samples characteristic calcium phosphate peaks could be detected.

The particles prepared with the variations of M3 are shown in FIG. 5'. The particles of (a) are fabricated using M3, showing no difference to M3-Sr, i.e. the version with 0.6 mM strontium (FIG. 1*c*). The particles in (b) from the solution with doubled ion concentrations, i.e. M3-Sr-2x, showed still spherical particles whereas the fivefold concentration, i.e. M3-Sr-5x, produced irregular shaped particles (c). The particles without carbonate (d) produced with M3-Sr-0$HCO_3^-$ were much smaller (<100 nm). XRD-analysis resulted in random patterns, which means that all particles of M3 are amorphous. One example of XRD-pattern is shown in FIG. 6'.

The use of M1 resulted in around 130 mg particle per litre D-PBS. Using M2 gave 180 mg particle per litre buffer solution and M3 produced 190 mg per litre solution. The differences in the productivity become even more evident if one considers the mass of particle per mass used salts. These productivities were around 13.3, 24.0 and 55.9 mg/g, respectively.

In FIG. 7' the curves of the strontium release study are displayed. The progressions of all curves are in a logarithmic shape. At the beginning the release proceeded very fast, so that at the first measuring point after around 15 min the strontium concentrations were already between 20 and 45% of the final concentration and after 2 days release the changes were minimal.

The released amount of strontium was dependant on the solution. Thereby the release was higher when the pH-value of the Tris-HCl solution was lower. The total amount of released strontium in the solutions after 13 days, shown in the following table, show that a pH-increase of 1.2 lowered the release to nearly 50%. Surprisingly, the release rate in D-PBS was much lower than those in Tris-HCl and the finally strontium concentration was 8.20 mg/g·l, thus less than a quarter of that in the Tris-HCl with the same pH-value.

TABLE 3

Cumulative release for Sr after 13 days.

| | mg/g · l | % |
|---|---|---|
| Tris-HCl 6.8 | 47.7 | 20.3 |
| Tris-HCl 7.4 | 35.5 | 15.3 |
| Tris-HCl 8.0 | 25.6 | 11.0 |
| D-PBS 7.4 | 8.2 | 3.5 |

Furthermore the released percentage of the total amount strontium in the particles was calculated by using the data of the composition of the particles as shown in the following table, achieved through the ICP measurements of the in HCl dissolved particle. In the pH 6.8 Tris-HCl 20.3% of the strontium was dissolved after 13 days, but in D-PBS just 3.5% of the strontium content of the spheres were detected in the solution (compare the above table).

TABLE 4

Composition of the powder from M1.

| | Sr | Mg | Ca | P |
|---|---|---|---|---|
| mg/g | 232.8 | 35.1 | 194.0 | 212.9 |

After ageing in Tris-HCl and D-PBS, respectively, at 37° C., the morphology of the particles from M1 changed slightly and signs of degradation were visible, but the particle shape was still spherical. However, there is no significant difference visible between the SEM pictures of the Tris-HCl experiments, as shown in FIG. 9*a-c* corresponding to Tris-HCl, pH 6.8, Tris-HCl, pH 7.4 and Tris HCl, pH 8.0, respectively. All particles show a porous surface and some even got deep cracks, especially visible in FIG. 9*a*. The particle that was aged in D-PBS, pH 7.4, shown in FIG. 9*d*, changed most in comparison with the picture of the original particle (FIG. 1*a*). Many particles got flakes or sheets on the surface, implying that not only degradation occur, but also a reformation and remodelling of the material. The pH-values of the solutions after the 13 days were measured to 6.75, 7.15, 7.75 and 7.45, thus, the pH-value of the Tris-HCl solutions decreased and that of the D-PBS increased slightly, but altogether these changes are negligible and the pH-value can be considered as constant.

Through the experiment M2-H2O, where the Tris-HCl buffer solution was replaced by water, the influence of the pH-value on the shape of the particles could be studied. This is due to that the pH-value does not remain constant over the whole reaction time without the buffer. This changing parameter could lead to the dominance of different processes and resulting in different morphologies. Hence, the particles from this method showed high diversity in morphology and size. From this result it can be gathered that the morphology of the particles could be controlled by adjusting the pH-value of the reaction solution, and perhaps as well by keeping it constant during the whole reaction or arranging specific changes of the pH-value. In the study about the influence of magnesium on the morphology of the spheres from M2, two different structural types could be detected and the critical concentration for the transition between these two seems to be around the composition of 0.38 mM Mg, where the picture shows a particle with a morphology being a mixture of the both characteristic shapes (FIG. 3'*e*). Likely the core of the flower-like particles is formed like the spheres with less magnesium and thereafter the flakes grew on the surface. This assumption is, however, not compatible with the results from the 1 h-experiments, which reveal that the nucleation of the particles is different. But nevertheless, it is possible that flakes grow on the surface of the rope-like structured spheres and thus a kind of the flower morphology results from the flurry nuclei. Additionally it was found that all the particles, regardless with which amount of Mg, had a CaP structure.

If one compares the results from all methods, it is clear that the liquid precursor affected the formation of the material. Strontium is a key factor for the formation of spheres in the D-PBS, but in M3 the addition of strontium had no visible influence, though carbonate was influential, and in M2 particles without strontium were still spherical shaped and magnesium had a bigger influence on the morphology than strontium. Furthermore, the morphology of the particles, prepared with solutions with same salt-composition and just a different buffer solution (M1, M2), is quite different (FIG. 1*b, c*), since the surface of the Tris-HCl particles was structured, but the PBS-particles had an even, only slightly dimpled surface, and in addition the latter one were shown to be hollow, but the spheres from M2 are solid.

In the methods described in this application changes of the morphology were observed, but the shape of the particles was always substantially spherical.

Since the particles from M3 are amorphous, the degradation of this particle will occur much faster than for M1 and M2. Thus, the particles formed by M3 is optionally heat treated, for example in an oven, to reach crystalline material. One method for the heat-treating is ripening in a solution where the particles are dispersed and thus the risk of agglomeration is smaller.

The special qualities for medical application of the prepared particle can be divided into two groups. The first is the release of the incorporated strontium that can be used to stimulate bone regeneration, imaginable would be local injection, and the second is the small size and spherical shape of the particles exhibit good qualifications for applications as carrier particles that are biocompatible. Its biocompatibility makes it suitable to circulate in the body and could, when functionalised, deliver adsorbed objects to exactly the place in the body were they are needed. This means that the loss of agent is smaller and the total dose of the active component can be reduced. For a good efficiency, high porous or even hollow particles with large specific surface area, respectively a large volume are advantageous, thus features that the particles from M1 and M2 provide. Imaginable applications are drug and gene delivery or usage as marker substance.

One application for the ion substituted CaP particles lies in products for dental care. Fluor is known to have advantageous properties in this application field. Strontium has as an effect against the hypersensitivity of teeth and the spherical shape of the particles fits furthermore good to close the dentinal tubes and therewith prevent fluid flow across them, which would decrease hypersensitivity and algesia.

Since the particles may have various cross-sectional shapes the term diameter is for the purpose of this application intended to refer to the effective diameter.

While the invention has been described in connection with what is presently considered to be the most practical and preferred embodiments, it is to be understood that the invention is not to be limited to the disclosed embodiments, on the contrary, it is intended to cover various modifications and equivalent arrangements within the appended claims.

Example 10

An animal study has been performed to investigate the effect of spherical Sr-substituted CaP (Sr—CP) particles on bone regeneration in a cavital bone defect model using example 1 with 0.6 mM Sr solution, the size of spheres was 100-1000 nm and the particles was spherical with a hollow core and a smooth shell.

Methods: The animals were pre-operated 12 weeks in advance of the material implant Pre-operation. Male Wistar rats weighing 500-600 were anestheised with 2L/min $O_2$, 400 $cm^3$/min $N_2O$, 200 $cm^3$/min halothan. The tail was washed three times with betadine and ligatured at the tail root for the prevention of bleeding. The tip of the tail was surgically removed and a defect was drilled through the distal side of the tail vertebra. With the dimensions of 2 mm in diameter and 3.5 mm in depth with a special driller tip that contained a stopper to standardize the depth of the defect. In order to stop the self-regeneration of the vertebra a kirschen wire was implanted into the hole. The wound was sutured using non-resorbable polypropylene monofilament 4/0 Premilene 45 cm suture. The localization of the kirschen wire was followed-up by X-ray. After twelve weeks was the animal anesthetised and washed by same procedure as mentioned above. The kirschen wire implant was removed.

Spherical Sr—CP powder was pre-mixed with 2 drops autologus blood prior to the use under sterile conditions. The defect was filled with the either Sr—CP (n=5), bone chips (n=5) or left empty (n=7) as a negative control and the wound was closed by same procedure as mentioned above. All surgical procedures was under aseptic condition. The animals were marked with incisions in their ears and eartags. To follow the bone ingrowth and regeneration of the bone Sr—CP, bone chips and empty defect was analysed by single isotope nanoSPECT-CT. NanoSPECT-CT was carried out once a week for six weeks and a final analysis at week 12. After twelve weeks the animals were overanesthetized and physical euthanised by exsanguation and the operated vertebra and the next healthy vertebra were surgically removed placed in 15 ml 4% formaldehyde and analyzed by microCT.

Results: After 12 weeks, trabecular bone was formed in the holedefects filled with using Sr—CP. Bony consolidation is enhanced, about 80% of the total defect volume was filled by the new formed bone. However, there is no bony consolidation in the holes fixed with bone chips. The results presented a good potential application of these spherical CaP particles as bone void filler material.

The invention claimed is:

1. A method for the formation of substantially spherical particles of an ion substituted calcium phosphate compound, comprising the steps of:

providing an aqueous solution comprising calcium, magnesium and phosphate ions, and one or more of sodium, potassium, chloride, carbonate or sulphate ions, wherein the concentration of said ions are: calcium ions in the range of $0.01\text{-}25\times10^{-3}$ M, magnesium ions in the range of $0.01\text{-}15\times10^{-3}$ M, and phosphate ions in the range of $0.01\text{-}10\times10^{-3}$ M, and when present, sodium ions in the range of $0.01\text{-}1420\times10^{-3}$ M, potassium ions in the range of $0.01\text{-}1420\times10^{-3}$ M, chloride ions in the range of $0.01\text{-}1030\times10^{-3}$ M, carbonate ions in the range of $0.01\text{-}270\times10^{-3}$ M, and sulphate ions in the range of $0.01\text{-}5\times10^{-3}$ M, wherein the solution has an initial pH in the range of 2.0 to 10.0, and wherein the solution further comprises at least one of substitution ions $Sr^{2+}$, $F^{-}$or $Si^{4+}$; and precipitating the particles by a self-organized process in a solution according to a, b, c, d or e, wherein:

a. is a static process wherein the solution comprises $Sr^{2+}$in a concentration of 0.15 mM to 0.6 mM, and wherein the solution has a temperature in the range of 37-60° C. to give spherical hollow particles, b. is a stirring process wherein the solution comprises $Sr^{2+}$in a concentration of 0.15 mM to 0.67 mM, and wherein the solution has a temperature in the range of 37-60° C. to give spherical hollow particles, c. is a hydrothermal process wherein the solution comprises $Sr^{2+}$in a concentration of 0.3 mM to 0.67 mM, and wherein the process is performed at a temperature range of 60° C. to 100° C. to give spherical particles with a dense shell and a porous core;

d. is a hydrothermal process wherein the solution comprises $F^{-}$in a concentration of 0.04 mM to 0.22 mM, and wherein the process is performed between 80° C. and 100° C. to give spherical porous particles; and e. is a hydrothermal process wherein the solution comprises $Si^{4+}$in a concentration of 6 mM to 10 mM, and wherein the process is performed between 80° C. and 100° C. to give spherical porous particles.

2. The method according to claim 1, wherein the Ca/P ratio of the formed spherical particles is in the range of 0.1 to 5.0.

3. The method according to claim 1, wherein the solution comprises $Mg^{2+}$at a concentration of 0.38-0.5 mM.

4. A particle obtained by a method for the formati of substantially spherical particles of an ion substituted calcium phosphate compound, the method comprising the steps of:

providing an aqueous solution comprising calcium, magnesium and phosphate ions, and one or more of sodium, potassium, chloride, carbonate or sulphate ions, wherein the concentration of said ions are: calcium ions in the range of $0.01\text{-}25\times10^{-3}$ M, magnesium ions in the range of $0.01\text{-}15\times10^{-3}$ M, and phosphate ions in the range of $0.01\text{-}10\times10^{-3}$ M, and when present, sodium ions in the range of $0.01\text{-}1420\times10^{-3}$ M, potassium ions in the range of $0.01\text{-}1420\times10^{-3}$ M, chloride ions in the range of $0.01\text{-}1030\times10^{-3}$ M, carbonate ions in the range of $0.01\text{-}270\times10^{-3}$ M, and sulphate ions in the range of $0.01\text{-}5\times10^{-3}$M, wherein the solution has an initial pH in the range of 2.0 to 10.0, and wherein the solution further comprises one of the substitution ions $Sr^{2+}$, $F^{-}$or $Si^{4+}$; and precipitating the particles by a self-organized process in a solution according to a, b, c, d or e wherein:

a. is a static process wherein the solution comprises $Sr^{2+}$in a concentration of 0.15 mM to 0.6 mM, and wherein the solution has a temperature in the range of 37-60° C. to give spherical hollow particles, b. is a stirring process wherein the solution comprises $Sr^{2+}$in a concentration of 0.15 mM to 0.67 mM, and wherein the solution has a temperature in the range of 37-60° C. to give spherical hollow particles, c. is a hydrothermal process wherein the solution comprises $Sr^{2+}$in a concentration of 0.3 mM to 0.67 mM, and wherein the process is performed at a temperature range of 60° C. to 100° C. to give spherical particles with a dense shell and a porous core;

d. is a hydrothermal process wherein the solution comprises $F^{-}$in a concentration of 0.04 mM to 0.22 mM, and wherein the process is performed between 80° C. and 100° C. to give spherical porous particles; and e. is a hydrothermal process wherein the solution comprises $Si^{4+}$in a concentration of 6 mM to 10 mM, and wherein the process is performed between 80° C. and 100° C. to give spherical porous particles.

5. The particle of claim 4, wherein the strontium concentration of the particle is between 0 to 35% by weight.

6. The particle of claim 4, wherein the magnesium concentration of the particle is between 0 and 10% by weight.

7. A method for delivering a component using the particle of claim 4, comprising filling hollows and/or pores of said particle with said component; or adsorbing or attaching said component to said particle, wherein said component is selected from the group consisting of drugs, contrast substances, radiolabled particles, genes, growth factors and ions.

8. A method of treating minimally invasive and preventative dental treatments or treatment of peridontitis, comprising administering to a subject in need thereof a composition comprising the particle of claim 4, wherein said composition is selected from the group consisting of: a cavity filling material; an implant material; adsorption agent for heavy metal ions; filler particles in toothpaste for healing of sensitive tooth roots, to improve sensitization and healing of early caries; dental tape or paste for healing of enamel, tooth paste, mouth water, mouth wash, mouth spray, tooth cream, bleaching and whitening pastes; food supplement and chewing gum.

9. A bone filler or bone growth stimulating composition, comprising the particle of claim 4, wherein the particle comprises $Sr^{2+}$as substitution ion and ion release.

10. A method for bone repair and regeneration or for tooth repair and regeneration, comprising administering to a subject in need thereof the particle of claim 4.

11. A composition comprising the particles of claim 4 for use in drug delivery applications, wherein the drug includes contrast substances and radiolabled particles;

or for us in delivery of genes or growth factors by filling the hollows and/or pores of the particles with said genes and/or growth factors or adsorbing said genes and/or growth factors to the particle surface;

or for use in controlled ion release.

12. A composition comprising the particles of claim 4 for use in dental minimally invasive and preventative treatments, treatment of peridontitis, or as a cavity filling material or as an implant material or as adsorption agent for heavy metal ions;

or in toothpaste for healing of sensitive tooth roots, to improve sensitization and healing of early caries; or as dental tape or paste for healing of enamel, tooth paste, mouth water, mouth wash, mouth spray, tooth cream, bleaching and whitening pastes;

or as food supplement and chewing gum;

or as a bone filler or in bone growth stimulating operations, wherein the particle comprises $Sr^{2+}$as substitution ion and ion release;

or for use in bone repair and regeneration, or for use in tooth repair and regeneration.

13. The method according to claim 1, wherein precipitating the particles by a self-organized process is a static process, wherein the solution comprises $Sr^{2+}$in a concentration of 0.15 mM to 0.6 mM, and wherein the solution has a temperature in the range of 37-60° C. to give spherical hollow particles.

14. The method according to claim 1, wherein precipitating the particles by a self-organized process is a stirring process, wherein the solution comprises $Sr^{2+}$in a concentration of 0.15 mM to 0.67 mM, and wherein the solution has a temperature in the range of 37-60° C. to give spherical hollow particles.

15. The method according to claim 1, wherein precipitating the particles by a self-organized process is a hydrothermal process, wherein the solution comprises $Sr^{2+}$in a concentration of 0.3 mM to 0.67 mM, and wherein the process is performed at a temperature range of 60° C. to 100° C. to give spherical particles with a dense shell and a porous core.

16. The method according to claim 1, wherein precipitating the particles by a self-organized process is a hydrothermal process, wherein the solution comprises $F^{-}$in a concentration of 0.04 mM to 0.22 mM, and wherein the process is performed between 80° C. and 100° C. to give spherical porous particles.

17. The method according to claim 1, wherein precipitating the particles by a self-organized process is a hydrothermal process, wherein the solution comprises $Si^{4+}$in a concentration of 6 mM to 10 mM, and wherein the process is performed between 80° C. and 100° C. to give spherical porous particles.

* * * * *